United States Patent [19]

Simons

[11] Patent Number: 5,851,762
[45] Date of Patent: Dec. 22, 1998

[54] GENOMIC MAPPING METHOD BY DIRECT HAPLOTYPING USING INTRON SEQUENCE ANALYSIS

[75] Inventor: Malcolm J. Simons, Glenluce, Australia

[73] Assignee: Gene Type AG, Switzerland

[21] Appl. No.: 293,779

[22] Filed: Aug. 22, 1994

Related U.S. Application Data

[63] Continuation of Ser. No. 971,856, Mar. 9, 1993, abandoned, which is a continuation-in-part of Ser. No. 550,939, Jul. 11, 1990, abandoned.
[51] Int. Cl.[6] .............................. C12Q 1/68; C12P 19/34
[52] U.S. Cl. ........................... 435/6; 435/91.1; 435/91.2; 435/91.53
[58] Field of Search .......................... 435/6, 91.53, 91.1, 435/91.2; 536/24.31

[56] References Cited

U.S. PATENT DOCUMENTS

| | | | |
|---|---|---|---|
| 4,683,202 | 7/1987 | Mullis ....................................... | 435/91 |
| 4,994,370 | 2/1991 | Silver et al. ................................ | 435/6 |
| 5,364,759 | 11/1994 | Caskey et al. .............................. | 435/6 |

FOREIGN PATENT DOCUMENTS

| | | |
|---|---|---|
| 16727/88 | 12/1988 | Australia . |
| WO 89/11547 | 11/1989 | WIPO . |
| WO 90/02818 | 3/1990 | WIPO . |
| WO 90/12891 | 11/1990 | WIPO . |

OTHER PUBLICATIONS

Brinster, et al. Proc. Natl. Acad. Sci. (1988) 85: 836–840.
Traver, et al. Proc. Natl. Acad. Sci. (1989) 86: 5898–5902.
Crenier, et al. Hun. Genet. (1988) 80: 235–246.
Nakamura, et al. Science (1987) 235: 1616–1620.
Burnside, et al. Endocrinology (1991) 128: 3183–3191.
Duyk, et al. Proc. Natl. Acad. Sci. (1990) 87: 8995–8999.
Weber et al. (1989) "Abundant class of human DNA polymorphisms which can be typed using polymerase chain reaction." Am. J. Hum. Gen. 44: 388–396.
Skolnick et al (1989) "Simultaneous analysis of multiple polymorphic loci. using amplified sequence polymorphisms (ASPo)." Genomics 2:273–279.
O'Hara et al (1988) "The human factor VII gene is polymorphic due to variation in repeat copy number in a minisatellite." Gene 66: 147–158.
Zhang et al. (1987) Structure of the mouse Adh-1 gene etc. Gene 57: 27–36.
Carmi et al., "Use of a DNA pooling strategy to identify a human obesity syndrome locus on chromosome 15", Human Molec. Genet. 4: 9–13, 1995.
Goto et al., "Genetic linkage of Werner's syndrome to five markers on chromosome 8", Nature 355: 735–738, Feb. 20, 1992.
Lander et al., "Homozygosity mapping: A way to map human recessive traits with the DNA of inbred children", Science 236: 1567–1570, Jun. 1987.
Arnheim et al., "Use of Pooled DNA Samples To Detect Linkage Disequilibrium of Polymorphic Restriction Fragments and Human Disease: Studies of the HLA Class II Loci," *Proc. Natl. Acad. Sci. USA* 82:6970–6974 (Oct. 1985).
Horn et al., "Characterization and Rapid Diagnostic Analysis of DNA Polymorphisms Closely Linked to the Cystic Fibrosis Locus," Clin.Chem. 36:1614, abstract (1990).
Clark, *Mol. Biol. Evol.* 7(2):111–122 (1990).
Dicker et al, *BioTechniques* 7:830–837 (1989).
Kerem et al, *Science* 245:1073–1079 (1989).
Mardis et al, *BioTechniques* 7:840–850 (1989).
Marx, *Science* 247:1540–1542 (1990).
Olson et al, *Science* 245:1434–1435 (1989).
Riordan et al, *Science* 245:1066–1072 (1989).
Rommens et al, *Science* 245:1059–1065 (1989).
Stephens et al, *Am. J. Hum. Genet.* 46:1149–1155 (1990).
DiLelia et al., *The Lancet,* i:497–499 (1988).
*Molecular Biology of the Cell,* Second Edition, New York, 1989, Chapter 9: "RNA Synthesis and RNA Processing" pp. 531–535 and Ch. 10: Control of Gene Expression pp. 602–604.
Boehnke et al, *Am. J. Hum. Genet.,* 45:21–32 (1989).
Cavalli–Sforza, L. *Am. J. Hum. Genet.* 46:649–651 (1990).
Seilhamer et al., *DNA,* vol. 3, No. 4, 309–317.
Geisel et al. Abstract No. 87082065; *J. Clin Chem Clin Biochem,* 26(7) 1988, 429–434 Biosis.
Funke et al. Abstract No. 84025060; *J. Clin Chem Clin Biochem,* 25(3) 1987, 131–134. Biosis.

*Primary Examiner*—Jasemine C. Chambers
*Assistant Examiner*—Scott D. Priebe
*Attorney, Agent, or Firm*—McCutchen, Doyle, Brown & Enersen, LLP

[57] ABSTRACT

The present invention is an improved genomic mapping method which is able to generate highly informative polymorphic sites throughout the genome. In addition to being highly polymorphic, the sites can be used to generate patterns that identify allelic and sub-allelic haplotypes associated with the region.

23 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 19 base pairs
        ( B ) TYPE: nucleic acid

```
          ( C ) STRANDEDNESS: double
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
              ( A ) ORGANISM: Homo sapiens
              ( D ) DEVELOPMENTAL STAGE: Adult ( v i i i ) POSITION IN GENOME:
              ( A ) CHROMOSOME/SEGMENT: 6

( x i ) SEQUENCE DESCRIPTION: SEQ ID NO:1:

TTCTGAGCCA GTCCTGAGA                                                                   1 9

( 2 ) INFORMATION FOR SEQ ID NO:2:

( i ) SEQUENCE CHARACTERISTICS:
              ( A ) LENGTH: 18 base pairs
              ( B ) TYPE: nucleic acid
              ( C ) STRANDEDNESS: double
              ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
              ( A ) ORGANISM: Homo sapiens ( v i i i ) POSITION IN GENOME:
              ( A ) CHROMOSOME/SEGMENT: 6

( x i ) SEQUENCE DESCRIPTION: SEQ ID NO:2:

GATCTGGGGA CCTCTTGG                                                                    1 8
```

GENOMIC MAPPING METHOD BY DIRECT HAPLOTYPING USING INTRON SEQUENCE ANALYSIS

This application is a continuation of U.S. application Ser. No. 07/971,856, filed Mar. 9, 1993 (now abandoned), which was a national phase application of International Application No. PCT/AU91/00310, filed Jul. 11, 1991, which was a continuation-in-part of U.S. application Ser. No. 07/550,939, filed Jul. 11, 1990 (now abandoned).

FIELD OF THE INVENTION

The present invention directly identifies haplotypes of individuals by analysis of non-coding sequence variation. This invention has a wide range of applications to rapidly test polymorphisms at specific sites throughout the genome and to expedite positional cloning of unknown human genetic disease genes identified by unique phenotypes.

BACKGROUND OF THE INVENTION

The cloned disease genes have been used to define the types of mutations causing human genetic disease (S. H. Orkin, et al *Ann. Rev. Genet* 18:131–171 (1984)), allowed the detection of abnormal genes prenatally (c.f. R. V. Lebo, et al *Am. J. Hum. Genet* 47:583–590 (1990)), and led to gene replacement therapy trials of those genes that can be introduced into the affected tissue (S. A. Rosenberg, et al *Human Gene Therapy* 1:73–92 (1990)). On the way to the goal of ultimately sequencing the entire human genome, the Human Genome Project will generate considerable mapping data and isolate and map RFLPs sequence tagged sites (STS), and cDNAs (ESTs; expressed sequence tags; M. D. Adams, et al *Sci.* 252:1651–1656 (1991)). Currently the most common method of identifying polymorphic markers is by restriction enzyme analysis using numerous restriction endonucleases. This process is labor intensive. This invention proposes to generate considerably more informative sites rapidly to expedite genome mapping, to identify unknown disease genes, and to provide information for prenatal diagnosis of at-risk fetuses.

HUMAN GENOME PROJECT

The Human Genome Project is a logical extension of individual efforts to map human genes and identify genes important to understanding development, tissue-specific expression and human genetic disease. The difficulty is in the large size and vast amount of information: each haploid genome received from each human parent has $3 \times 10^9$ basepairs of DNA. The initial long term goal of the Genome Project is to sequence each basepair from a normal person(s). Individual scientists with related projects are expanding the scope and cost of the project by including other related goals. The initial first step was to generate a map of polymorphic linked loci at about 10 centimorgans throughout the genome. Several 10 centimorgan maps of individual chromosomes have been generated and a couple of chromosomes are nearing a 1 centimorgan map. In the meantime, the most dense polymorphic maps generated are in the regions of unknown disease genes with uniquely distinguishable phenotypes. Positional cloning projects have succeeded in identifying about a dozen unknown disease genes (see below) and have produced high density maps in the disease gene regions. The most useful markers in generating chromosome linkage maps are those polymorphic markers with many alleles that are informative in nearly every mating. These sites make the adjacent sites with fewer informative matings more informative. This invention proposes a means to develop considerably more informative polymorphic sites as anchor points for linkage studies.

PRENATAL DIAGNOSIS OF CLONED DISEASE GENES

About a dozen disease genes have been cloned based upon the known gene product like hemoglobin or clotting factor. Another dozen genes have been isolated by positional cloning. Initially prenatal diagnosis is offered based on the segregation of informative polymorphisms in the disease gene region. Standard RFLP analysis that identify enough informative polymorphisms to assure diagnoses in nearly each case can be more (R. V. Lebo, et al *Am. J. Hum. Genet* 47:583–590 (1990)) or less labor intensive. When a limited number of gene mutation result in most of the disease-causing sequence changes at any given locus, then specific probes for each mutation account for a significant portion of the disease alleles, polymorphic analysis of the abnormal haplotypes may be the only available option. Currently this is the case for cystic fibrosis with its many reported mutated alleles. However, use of a method that provides much more informative polymorphic sites which are screened than the present methods would expedite the ability to implement prenatal analysis.

"Reverse genetics" or "positional cloning" of an unknown disease gene refers to the process of moving toward a genetic disease locus by ever closer flanking polymorphic markers that recombine ever less frequently until candidate genes can be isolated and sequenced in patients and normal subjects. The disease gene has been identified when all mutant alleles can be shown to have a disease-causing alteration (c.f. S. H. Orkin, et al *Ann. Rev. Genet.* 18:131–171 (1984)) and all normal alleles have normal sequences. The first part of the search sifts through many polymorphic markers throughout the genome until a polymorphism is found to give a LOD (log of the odds) score greater than 2. Then, more markers are tested until a LOD score of 3 is obtained, and the linkage is considered proven. This means the likelihood that the polymorphic site is linked to the gene is greater than 999/1000 ($\log_{10} 1000=3$; $10^3 =1000$). Ray White's laboratory finds that, as expected, about 1 putative linkage out of 1000 tested with LOD scores greater than 3.0 is unlinked.

The entire genome is estimated to include about 3000 centimorgans (1 centimorgan=1% recombination) on the 22 pairs of autosomes and one pair of sex determining chromosomes. Ideally one would have available about 300 evenly spaced very polymorphic sites at 10 cM intervals throughout the entire genome so that each search of the genome for linkage to a disease gene would reveal linkage between one informative polymorphic marker and the disease phenotype. Unfortunately only some chromosomes have well mapped polymorphic markers. Those markers are not evenly spaced on the chromosomes. Therefore, current genome searches for a linked polymorphic marker typically include about 1200 polymorphic probes that test about 85% of the total human genome. The more informative the chromosome site, the more useful.

One goal of the human genome project is to develop evenly spaced, very polymorphic sites so that additional disease genes can be mapped readily using the fewest number of markers and patients possible. Isolating and mapping cDNAs from tissue-specific libraries will provide additional unique mapped chromosome sites as well as candidate genes for genetic diseases (M. D. Adams et al *Sci.* 252:1651–1656 (1991)). Once located, a search for informative polymorphic markers at that chromosome site is required so that segregation analysis between disease gene phenotypes and/or other polymorphic sites can add the locus to a genetic (linkage) map or test the site as a candidate gene.

Another trend is that the predicted number of centimorgans based upon counting chiasma (recombinations) in early metaphase of male meiosis has underestimated the number of centimorgans in thoroughly studied chromosomes. For instance, chromosome 1 had been estimated to be 200 to 300 centimorgans, but the genetic distance has now been demonstrated to be about 464 centimorgans to the most distal polymorphic sites tested. Therefore the number of polymorphic probes may have to be even greater than previously estimated to screen the entire genome for an unknown genetic disease phenotype.

The number of affected patients and their families required prior to initiating a positional cloning project depends upon the mode of inheritance. Another factor is the probability that a polymorphic marker associated with the probe will only be informative in a portion of the matings. A good patient population to study for an autosomal recessive genetic disease is 20 families with two living children affected with the disease. This allows the investigator to determine the phase of the disease phenotype and polymorphic locus in all informative patients and the first affected child and to compare the rate of recombination in the second child. For autosomal dominant genetic diseases, a single large pedigree may have 10 informative meioses so that two such pedigrees will be sufficient for testing. This number of subjects can be expected to give a LOD score between +2.0 and +3.0 for an informative polymorphic marker with a minor allele frequency of 30% (the major allele frequency of a two allele system is then 70%). For all polymorphic sites that give LOD scores greater than +2.0, linkage is tested with more polymorphic probes in this chromosome region. For all probes with LOD scores less than −2.0 (chance of linkage is less than $1/100=10^{-2}$), linkage is considered to be excluded.

When a genetic disease is mapped to a unique chromosome region with a LOD score of 3, other polymorphic markers in that chromosome region are tested and the results compared by multipoint linkage analysis on computer programs like LIPED developed by Jurg Ott. Multipoint analysis increases the likelihood that the linkage is correct by raising the LOD score (perhaps to 4.0 so that the likelihood of linkage is 9,999/10,000) or often quickly excludes this chromosome region by revealing double recombinants in smaller chromosome regions that lower the LOD score precipitously.

It is noted that a positional cloning project should not be initiated unless the clinical status of each family member can be determined with a high degree of certainty. An exception to this rule occurred when the "depression" locus was reported to segregate with the short arm of chromosome 11 (chromosome 11p) in the Amish. In this instance, it was discovered that the phenotype analysis on which the linkage study was based was incorrect when two patients promptly developed severe depression shortly after the LOD scores with chromosome 11p polymorphisms were reported to be greater than 6 (the odds of linkage are greater and 1,000,000/1,000,001). When the LOD scores were calculated based on correctly assigning these two phenotypes, the correlation disproved the linkage. This development has made population geneticists more skeptical than necessary for easily diagnosed diseases, but emphasizes the importance of a correct clinical diagnosis in each family member on which the linkage studies are based.

When a disease gene has been mapped to a linked polymorphic probe, the next step is to isolate and test the segregation of many other polymorphic markers in the same chromosome region. Obtaining existing markers depends upon the clones and libraries available from previous studies of the same chromosome region or available cDNAs or other very polymorphic probes previously mapped to this chromosome region. The optimal strategy for generating new probes depends upon collaborating laboratories' resources and expertise.

For instance, somatic rodent-human hybrid cells carrying the whole human chromosome to which the disease gene has been mapped can be irradiated. Then cell strains carrying only the chromosome region with the linked polymorphic probe can be isolated. Recombinant libraries are screened with human alu repetitive sequences to identify the human clones. This identifies many human clones because the alu sequence is repeated about 300,000 times throughout the human genome. From these clones DNA polymorphic sites can be identified, and further linkage analysis done in the families.

A second approach is to dissect a portion of the chromosome in the disease gene region, amplify the few collected chromosome segments with alu primers, and clone the amplified fragments. These fragments are then used to find polymorphisms in the disease gene region. The segregation of these polymorphic sites are tested in all affected pedigrees to further define the disease gene region. Dissected libraries have been made in about a dozen known genetic disease loci.

Simultaneously other cloned genes mapped to the putative disease gene region can be tested for polymorphisms and the segregation of these genes tested in affected pedigrees.

At this point a clinical prenatal genetic test might be offered that is 95% reliable and informative in at least 75% of the cases as defined in R. V. Lebo, et al *Am. J. Hum. Genet.* 47:583–590 (1990). Depending upon the frequency of the genetic disease, the patient population may be limited to merely mapping the location of the disease gene and finding closely linked genetic markers. Other than identifying the alteration in the gene this might be the case for perhaps 2,000 of the over 4,000 genetic diseases described (McKusick, Mendelian Inheritance in Man).

The next goal of positional cloning is to delineate an unknown genetic disease locus between flanking markers that span no more than 1 megabase (Mg) or 1,000,000 basepairs of DNA. The continuing process of screening ever greater numbers of cloned DNA fragments in such small chromosome regions while minimizing the number of clones tested outside the region is the most productive. For instance, cosmid clones isolated from irradiated chromosome 17 hybrids and identifying clones on the long arm by hybridization to hybrids carrying only that chromosome region were used to saturate the neurofibromatosis-1 gene locus. Then again, a library of fragments from the cystic fibrosis chromosome region was made from a cell line carrying a nearby selectable gene that was retained in all hybrid cell strains.

About a dozen disease genes have been identified by positional cloning including Duchenne muscular dystrophy (A. P. Monaco, et al, *Nature* 323:646–650 (1986)) and chronic granulomatous disease (B. Royer-Pokora, et al *Cold Sp. Harbor Symp. LI*:169–176 (1986)) on the X chromosome, cystic fibrosis (J. M. Rommens, et al *Sci.* 245:1059–1065 (1989); J. R. Riordan, et al *Sci.* 245:1066–1073 (1989); B. S. Kerem, et al *Sci.* 245:1073–1080 (1989)) on chromosome 7, and neurofibromatosis-1 on chromosome 17 (M. R. Wallace, et al *Sci.* 249:181–186 (1990)). The X chromosome genes and the neurofibromatosis-1 locus on chromosome 17 were identified more easily and quickly because chromosome rearrangements defined the disease gene region. More effort was required to delimit the cystic fibrosis gene, an autosomal recessive genetic disease to a megabase region with flanking markers by linkage analysis and disequilibrium. Then chromosome hopping with yeast artificial chromosome (YAC) libraries was used to isolate the remaining DNA segments prior to identifying the abnormal gene with YAC "hopping" and "linking" libraries (J. M. Rommens, et al Sci. 245:1059–1065 (1989).

Then transcribed genes in the putative disease gene region may be identified by searching for conserved sequences between species, looking for CpG islands with restriction endonuclease cut sites, and a recently developed exon trapping protocol. YAC clones are partially digested and subcloned in cosmids. Then the cosmids are labeled, preannealed to total unlabeled human DNA to hybridize to the repetitive sequences, and then hybridized to Souther blots of DNAs from dog, mouse, cat, and cow (referred to as zoo blots). YAC clones that carry sequences that hybridize to each are considered to carry conserved genes. These cosmids are then used to screen a tissue specific cDNA library. These cosmids recognizing homologous cDNA clones are then hybridized to Northern blots of different tissues to determine whether the putative gene is expressed in the affected tissue. Such tissues can come from a human cadaver or a laboratory rat.

A second approach to identify genes is to cut YAC clones with enzymes like BssHII, EagI and SacII that recognize and cut CpG islands 5' to many genes (C. A. Sargent et al EMBO 8:2305–2312 (1989)). The isolated YAC clones can be digested and separated using pulsed field gel electrophoresis to learn whether any YAC inserts have been cut. Then the ends of the cut fragments can be isolated by ligating to plasmid vectors, digesting with an restriction enzyme that does not cut the vector, and transforming bacteria that require the plasmid to grow, just as the NotI YAC linking libraries were constructed. Plasmids that grow are used to screen zoo blots for conserved sequences, Northern blots of tissue extracts, and cDNA libraries.

A third approach, Exon Trapping, has been developed by Dr. Geoffrey Duyk, who used retroviral vectors to help characterize gene regions. YAC or cosmid cloned sequences are digested and shotgun cloned into retroviral vector pETV-SD carrying an exon trap cassette. This Exon Trap vector identifies functional splice acceptor sites encoded in cloned genomic DNA fragments. Since most genes undergo RNA splicing, such sites serve as identifiers for most genes. Pooled plasmid DNA from this shotgun cloning is transfected into an ecotropic retroviral packaging cell line. This cell line provides proteins required for vector propagation as a retrovirus. Retroviral DNA is transcribed in vivo and transcripts with functional splice sites may undergo splicing with loss of the marked intervening sequence in the cassette. Spliced and unspliced viral RNAs are packaged into virions, harvested from this culture, and used to infect COS cells. This second replication increases the splicing frequency. Virus isolated from this second culture is used to infect COS cells that constitutively produce SV40 antigen. Thus the shuttle vector is reverse transcribed and amplified as a circular DNA episome with an SV40 origin or replication in the vector. The β-galactosidase indicator gene is excised by splicing and results in a white colony whereas colonies that are not spliced are usually blue. Splicing events are verified in white colonies by DNA sequencing primed from within the splice donor exon. These candidate exons are used to screen zoo blots, cDNA libraries, or Northern blots to potentially identify genes.

DESCRIPTION OF THE PRIOR ART

Marx, Science 247:1540–1542 (1990) reports on the challenge that geneticists face in understanding components of multi-cause diseases such as autoimmune diseases, high blood pressure, obesity, cancer and mental diseases including Alzheimer's disease, manic depression, and schizophrenia.

Olson et al, Science 245:1434–1435 (1989) reports a suggestion for a physical mapping system using sequence-tagged sites to provide a common language for genomic mapping.

A series of three articles [Rommens et al, Science 245:1059–1065 (1989), Riordan et al, Science 245:1066–1072 (1989) and Kerem et al, Science 245:1073–1079 (1989) report a new gene analysis method called "jumping" used to identify the location of the CF gene, the sequence of the CF gene, and the defect in the gene and its percentage in the disease population, respectively.

DiLelia et al, The Lancet i:497–499 (1988) describes a screening method for detecting the two major alleles responsible for phenylketonuria in Caucasians of Northern European descent. The mutations, located at about the center of exon 12 and at the exon 12 junction with intervening sequence 12 are detected by PCR amplification of a 245 bp region of exon 12 and flanking intervening sequences. The amplified sequence encompasses both mutations and is analyzed using probes specific for each of the alleles (without prior electrophoretic separation).

Dicker et al, BioTechniques 7:830–837 (1989) and Mardis et al, BioTechniques 7:840–850 (1989) report on automated techniques for sequencing of DNA sequences, particularly PCR-generated sequences.

Clark, Mol. Biol. Evol., 7(2):111–122 (1990) describes an algorithm which can be used in some cases to infer haplotypes from PCR-generated allele determinations or to infer haplotype frequencies of closely linked restriction site polymorphisms.

Stephens et al., Am. J. Hum. Genet., 46:1149–1155 (1990) describe a method for determining haplotypes of multiply heterozygous individuals. The method, referred to as "single-molecule-dilution" or "SDM", relies on stochastic separation of single-stranded DNA molecules by sufficient dilution to reliably include only one molecule of DNA in each diluted sample. Upon obtaining a single strand of DNA, the PCR technique is used to analyze the haplotype of the molecule.

Another method for direct identification of haplotypes is described by Boehnke et al, Am. J. Hum. Genet. 45:21–32 (1989). The method performs the analysis using haploid cells, specifically sperm cells.

Cavalli-Sforza, Am. J. Hum. Genet. 46:649–651 (1990) proposes that a statistical sampling of the genome of numerous individuals at various genetic locations be made as part of the genome mapping project to provide information as to the degree of individual variation present in the genome.

Each of the above-described references is incorporated herein by reference in its entirety.

SUMMARY OF THE INVENTION

The present mapping method utilizes direct determination of haplotypes through analysis of an individual's genomic DNA. The present mapping method provides a way to obtain information regarding the amount of polymorphism associated with any genetic region of interest and to identify individuals having different alleles and haplotypes for the genetic region. In addition, the method provides information as to the distance and direction of a gene of interest, particularly a disease gene, from a given genetic locus. This method is particularly useful for locating disease genes that are not associated with chromosomal rearrangements.

The method also provides a rapid way to generate polymorphic markers throughout the genome, particularly in any genetic locus of interest. Not only can the markers be identified and screened more readily than classical RFLP sites, but the markers are much more informative than classical RFLP sites, which are either present or absent at any given location.

The present invention is based on the finding that non-coding region sequences, particularly intron sequences, contain genetic variations that are characteristic of alleles of adjacent and remote, linked genetic loci on the chromosome. In particular, primer-defined, amplified DNA sequences that include a sufficient number of intron sequence nucleotides can be used to produce patterns which are characteristic of alleles and haplotypes associated with a genetic region of interest. The patterns can be produced by gel electrophoresis length differences in the amplified DNA sequences or can be RFLP fragment patterns produced by digestion of the amplified DNA sequences with one or more endonucleases. Alternatively, once sufficient sequence information has been obtained, allele/haplotype-specific amplification can be used to detect the presence of the selected allele/haplotype.

The mapping method provides information about the degree of polymorphism of a genetic locus by determining the number of allelic and sub-allelic (haplotypic) patterns produced for the locus by analyzing the DNA of numerous individuals. The method can be used to screen individuals to explore individual variation associated with a genetic locus of interest. The method also provides information regarding disease-associated genetic loci that can be used to study the population genetics of a disease, particularly monogenic disease.

DETAILED DESCRIPTION OF THE INVENTION

The present invention is an improved mapping method which is based on the ability to identify haplotypes of individuals through analysis of non-coding region sequence variation patterns, particularly intron sequence variation patterns. The mapping method has two aspects. First, for any particular region of interest, the method provides information regarding the degree of polymorphism associated with the region and identifies those individuals with differing allelic and sub-allelic (haplotypic) sequences, enabling characterization of individual variability throughout a population. For a particular region of interest, such characterization avoids repetitive sequencing of individuals with the same genetic sequence.

By analyzing haplotype restriction associated with a region of interest, one can determine the direction of and, ultimately, the location of a gene of interest. In addition, direct haplotyping facilitates locating a disease-associated gene of interest without the need to resort to linkage analysis based on family studies. Direct analysis of haplotypes of normals and of those affected by the disease can be performed to identify the locus associated with a disease.

Second, the method provides a rapid way to generate and screen polymorphic markers throughout the genome. In particular, non-coding sequences in any region for which there is about 200 to 500 nt of sequence information, particularly at a genetic locus, can be rapidly amplified and analyzed, and thus provide a marker which can be economically screened. In addition, the markers are much more informative than classical RFLP sites, which are either present or absent at any given location. For every genetic locus, analysis of one or a few intron sequence markers can identify the alleles/haplotypes associated with the locus. For intergenic sequences, the degree of polymorphism associated with the region is even higher.

The present invention is based on the discovery that amplification of primer-defined DNA sequences that include a sufficient number of non-coding sequence nucleotides, particularly intron sequence nucleotides, can be used to produce patterns which are characteristic of alleles and haplotypes associated with a genetic region of interest. The present method reads haplotypes as the direct output of the DNA typing analysis when a single, individual organism is tested. The method is described herein in terms of mapping the human genome. However, the method is generally applicable to all eukaryotes. The method is preferably used for mapping genomic DNA of plant and animal species.

Definitions

The term "allele", as used herein, means a genetic variation associated with a coding region; that is, an alternative form of the gene. Such variations include "silent" variations which do not result in the substitution of an amino acid in the encoded protein.

The term "linkage", as used herein, refers to the degree to which regions of genomic DNA are inherited together. Regions on different chromosomes do not exhibit linkage and are inherited together 50% of the time. Adjacent genes that are always inherited together exhibit 100% linkage.

The term "linkage disequilibrium", as used herein, refers to the co-occurrence of two alleles at linked loci such that the frequency of the co-occurrence of the alleles is greater than would be expected from the separate frequencies of occurrence of each allele. Alleles that co-occur with frequencies expected from their separate frequencies are said to be in "linkage equilibrium".

As used herein, "haplotype" is a region of genomic DNA on a chromosome which is bounded by recombination sites such that genetic loci within a haplotypic region are usually inherited as a unit. However, occasionally, genetic rearrangements may occur within a haplotype. Thus, the term haplotype is an operational term that refers to the occurrence on a chromosome of linked loci.

As used herein, the term "intron" refers to untranslated DNA sequences between exons. The 5' flanking region including the promoter and 3' flanking region associated with a gene are referred to as a gene locus. The term "intergenic sequence" is used to refer to the spacing sequences between genetic loci which are not associated with a coding region and are colloquially referred to as "junk".

As used herein, the term "amplified DNA sequence" refers to DNA sequences which are copies of a portion of a DNA sequence and its complementary sequence, which copies correspond in nucleotide sequence to the original DNA sequence and its complementary sequence.

The term "complement", as used herein, refers to a DNA sequence that is complementary to a specified DNA sequence.

The term "primer site", as used herein, refers to the area of the target DNA to which a primer hybridizes.

The term "primer pair", as used herein, means a set of primers including a 5' upstream primer that hybridizes with the 5' end of the DNA sequence to be amplified and a 3', downstream primer that hybridizes with the complement of the 3' end of the sequence to be amplified.

The term "exon-limited primers", as used herein, means a primer pair having primers located within or just outside of an exon in a conserved portion of the intron, which primers amplify a DNA sequence which includes an exon or a portion thereof and not more than a small, para-exonic region of the adjacent intron(s).

The term "intron-spanning primers", as used herein, means a primer pair that amplifies at least a portion of one intron, which amplified intron region includes sequences which are not conserved. The intron-spanning primers can be located in conserved regions of the introns or in adjacent, upstream and/or downstream exon sequences.

The term "genetic locus", as used herein, means the region of the genomic DNA that includes the gene that encodes a protein including any upstream or downstream transcribed noncoding regions and associated regulatory regions. Therefore, an HLA locus is the region of the genomic DNA that includes the gene that encodes an HLA gene product.

As used herein, the term "adjacent locus" refers to either (1) the locus in which a DNA sequence is located or (2) the nearest upstream or downstream genetic locus for intron DNA sequences not associated with a genetic locus.

As used herein, the term "remote locus" refers to either (1) a locus which is upstream or downstream from the locus in which a DNA sequence is located or (2) for intron sequences not associated with a genetic locus, a locus which is upstream or downstream from the nearest upstream or downstream genetic locus to the intron sequence.

The term "locus-specific primer", as used herein, means a primer that specifically hybridizes with a portion of the stated gene locus or its complementary strand and does not hybridize with other DNA sequences under the conditions used in the amplification method. A locus-specific primer pair defines an amplified DNA sequence that is present in a plurality of alleles of a genetic locus or all alleles of the locus. The locus-specific primer pair contains one locus-specific primer. The other primer of the pair can be common to a multiplicity of genetic loci or can also be a locus-specific primer.

The term "sequence-specific primer" (SSP), as used herein, means a primer that specifically hybridizes with a sequence polymorphism present in one or more alleles of a genetic locus or their complementary strands but not present in all the alleles of the locus. The SSP does not hybridize with alleles of the genetic locus that do not contain the sequence polymorphism under the conditions used in the amplification method. A sequence-specific primer pair defines an amplified DNA sequence that is present in a number of alleles of a genetic locus but not in all alleles of the locus. The sequence-specific primer pair contains one sequence-specific primer. The other primer of the pair can be common to a multiplicity of primer pairs for the genetic locus or can also be a specific for the same group of alleles as the sequence-specific primer.

The term "allele-specific primer" (ASP), as used herein, means a primer that specifically hybridizes with a sequence polymorphism present in one allele of a genetic locus or its complementary strand and not present in other alleles of the locus. The ASP does not hybridize with other alleles of the genetic locus under the conditions used in the amplification method. An allele-specific primer pair defines an amplified DNA sequence that is present in one allele of a genetic locus and is not present in other alleles of the locus. The allele-specific primer pair contains at least one allele-specific primer. The other primer can be common to a plurality of alleles.

The term "haplotype-specific primer" (HSP), as used herein, means a primer that specifically hybridizes with a sequence polymorphism present in one haplotype associated with a genetic locus and one or more adjacent loci or its complementary strand and not present in other haplotypes associated with the locus. The HSP does not hybridize with other haplotypes of the genetic locus under the conditions used in the amplification method. A haplotype-specific primer pair defines an amplified DNA sequence that is present in one haplotype associated with a genetic locus and is not present in other haplotypes associated with the locus. The haplotype-specific primer pair contains at least one haplotype-specific primer. The other primer can be common to a plurality of haplotypes associated with the genetic locus and its adjacent loci or can also be a haplotype-specific primer.

As used herein, the terms "endonuclease" and "restriction endonuclease" refer to an enzyme that cuts double-stranded DNA having a particular nucleotide sequence. The specificities of numerous endonucleases are well known and can be found in a variety of publications, e.g. *Molecular Cloning: A Laboratory Manual* by Maniatis et al, Cold Spring Harbor Laboratory 1982. That manual is incorporated herein by reference in its entirety.

The term "restriction fragment length polymorphism" (or RFLP), as used herein, refers to differences in DNA nucleotide sequences that produce fragments of different lengths when cleaved by a restriction endonuclease.

The term "HLA DNA", as used herein, means DNA that includes the genes that encode HLA antigens. HLA DNA is found in all nucleated human cells.

Analysis of Non-coding Sequence Variation

Studies of non-coding sequence variation at loci of the HLA gene complex have revealed a stellar array of polymorphic variability that can be used to discern the evolution of the loci of this complex and study linkage disequilibrium between closely linked genetic disease loci and unique HLA haplotypes. Most gene loci are more conserved than those of the HLA complex in which polymorphic variability is maximized. This is because conservation of most gene loci is necessary for survival. Thus the HLA region can serve as a paradigm for polymorphism throughout the genome for approaches to analysis of allelic variation within each gene locus. Linkage disequilibrium reflects the cosegregation of very close chromosome regions through many generations. Linkage disequilibrium is the opposite extreme of linkage equilibrium which reflects the random segregation of genes on difference chromosomes or in distant chromosome regions. The considerable allelic variability at each locus can be used to assess the segregation of polymorphisms at neighboring gene loci for the generation of high resolution linkage maps by detecting significant linkage disequilibrium between alleles of loci in linked regions extending over one or more megabases.

The prior art describes numerous instances where polymorphic loci are used to study the frequency of cosegregation of other linked polymorphic loci or genes in human pedigrees as described in the background section. In every instance where polymorphisms were used, analysis of noncoding sequence variation of this invention can be applied. The applicability in the HLA region with its highly variable alleles demonstrates that other non-coding gene sequences will be informative and will increase the power of each method of analysis proportionally with the increase in the number of informative matings at each locus.

For instance, few RFLPs have more than 3 alleles identified by any restriction enzyme. Those RFLPs with 6 or more alleles are informative in almost every mating so that these loci serve as anchor points along a chromosome for other restriction enzyme results. Each anchor point increases the information derived from the flanking polymorphic alleles because these less informative locations cannot be compared with each other as often as with the anchor point. The marker sites of this invention will provide more anchor points that can be tested more rapidly for less effort.

Anchor points can be derived most easily from chromosomally sublocalized cDNA clones that by definition represent exons with the intervening sequences spliced out. Primers can be synthesized in different regions of the cDNA and used to amplify non-coding sequences to test for allelic variability in the different introns. Introns less than 2 kb are most easily amplified. When reverse genetic projects isolate putative genes by screening zoo blots, cDNA libraries, or by cloning restriction sites, the gene sequences can be analyzed and tested for polymorphisms using the present method.

A similar or greater level of variability is found in intergenic regions because less selective pressure is maintained in these regions than for active genes. Therefore those sequences can also be used for the location of the markers of this invention.

More specifically, using the methods and reagents of this invention, two types of non-coding sequence variation associated with genetic loci and intergenic sequences have been found. The first is allele-associated variation. That is, the non-coding sequence variation pattern associates with the allele type at an adjacent locus. The second type of variation is suballelic variation associated with alleles of remote linked loci (haplotypes). That is, sequence variations are present in a sub-population of individuals with the same allele. This sub-allelic variation is associated with alleles at remote loci (haplotypes). Such haplotypic differences may occur between sequences characterized as having the same haplotype. Such individual-limited or individual-specific variation is not common.

Furthermore, an amplified DNA sequence that contains sufficient non-coding sequences, preferably intron sequences, will vary depending on the allele/haplotype-associated sequence present in the sample DNA. That is, the non-coding sequence, particularly the introns, contain genetic variations (e.g.; changes in the number or location of restriction sites or gel electrophoresis length polymorphisms due to insertions, deletions and/or sequence substitutions that effect electrophoretic mobility) which are associated with alleles at adjacent and remote loci.

These non-coding sequence variation patterns can be generated anywhere there is about 200 to 500 bp of sequence information. In particular, the sites can be generated within cDNA gene sequences, within STS sites and within known classical RFLP sites. Of these locations, most preferred is the generation of intron variation sites within genes. The number of cloned genes stood at 945 in 1989, so there are numerous loci that can be used. In addition, when a region of the genome is of particular interest, there are techniques for identifying additional genes within the region. For example, in cases where a genetic disease locus is mapped to a unique chromosomal region with a LOD score of 3 or more (a region of about one megabase of DNA containing about 20 genes), any of the prior art techniques; e.g. exon trapping and zoo blot analysis, can be used in the region to identify additional genes within the region. Once additional genetic loci in the region are identified, other intron variation markers in the newly identified loci can be developed as described hereinafter.

As stated previously, these polymorphic variation patterns can be readily identified for any genetic locus. Furthermore, the patterns are readily produced and analyzed for rapid screening. In addition, the patterns are highly informative so that the screening provides much more information than classical RFLP sites. This combination makes intron variation patterns ideal markers for expeditious mapping of disease-associated gene loci.

In particular, one of the goals of the genome mapping project is to produce dense, evenly spaced markers throughout the genome. As stated previously, the usefulness of a marker is directly related to the degree of polymorphism of the marker.

The intron variation patterns generated by the present method can be used to facilitate this process. Specifically, amplified intron sequences can generate a physical and genetic map that is more dense and more informative for genome searches than prior art maps using less informative markers. The intron-containing, amplified DNA sequences of this invention from unique gene regions provide easily screened and very informative markers that directly provide allele and haplotype information about the locus. In addition to being easily screened and highly informative, the intron variation patterns can be generated and scored faster and less expensively than classical RFLP patterns. This is of particular value in providing the most information in the shortest time for the least cost. In light of the likelihood that the genome is larger than presently estimated, and of the large costs and limited funding for the genome project, use of a method that provides more information in a short period of time is particularly advantageous. In addition, it is anticipated that the genes will be more evenly distributed along the length of a chromosome than empirically determined RFLP sites.

It is estimated that there will be 50,000 genes throughout the human genome. Concentrating the initial activity on mapping and studying gene sequences, rather than intergenic sequences reveals many more candidate disease genes to facilitate matching genes to genetic diseases. Since genes are estimated to represent about two percent of the genome, this is an effective initial approach that identifies genes as the part of obtaining the initial information to produce polymorphic sites. The polymorphic marker sites of this invention can be produced in any of the known genetic loci.

In addition to identifying sequence polymorphism patterns in a gene, any other region for which there are at least 200, preferably at least 500 bp of sequence information can also be used as a marker site to produce amplified DNA sequences that produce patterns that identify alleles/haplotypes associated with the region. As stated previously, when locating polymorphic pattern sites, either genetic locus, STS, or RFLP sites can be used to provide markers. The non-coding polymorphic variation patterns of this invention are at least as effective as screening for CA and GA repeats throughout the genome at STS sites in terms of the limited cost and time required for screening in comparison to classical RFLP analyses. In addition, polymorphic variation patterns of this invention can be substituted for RFLP sites in any mapping technique where isolated cDNAs have been mapped to the same chromosome region. In addition to providing more informative polymorphic markers for use in any of the prior art mapping and linkage analysis methods, the haplotypic patterns for a region can then be used to generate a haplocontig map, as described below.

Once the haplotypes for a region are determined, the haplotypes for a distant region (about 0.01 to 2 million basepairs [Mbp] away) from the first locus are then analyzed in the same manner. The next region to be analyzed is preferably sufficiently close to provide some haplotypic patterns characterized by PDLP or RFLP patterns which are shared with the previous locus. That is, there will be patterns for some of the same haplotypes at an adjacent locus. By analyzing the haplotypic patterns at a given location, the location of genetic loci and of haplotypic regions can be identified. This identification can localize the borders of linked loci and of the haplotypic regions. In this way, contiguous overlapping haplotypic regions (haplocontigs) can be analyzed to form a map.

Analysis of the patterns of intron variation for a particular group of individuals can identify both the alleles and sub-typic or sub-allelic groups (haplotypes) at that locus present in members of the group. By analyzing a groups of individuals representing the greatest ethnic diversity among humans and greatest breed and species variety in plants and animals, patterns characteristic of the most common alleles/ haplotypes of the locus can be identified. Additional allelic and haplotypic patterns can be identified by screening larger populations. In this way the degree of polymorphism in alleles/haplotypes associated with any locus of interest can be determined without the need to perform repetitive sequencing of numerous individuals.

Rather than generating a map, the haplotypic pattern can be used to identify the direction of any gene of interest. Such genes include disease-associated genes and, in plants and animals, commercially desireable trait loci. For example, analysis of haplotypic patterns of patients with a disease, particularly a monogenic disease, produces patterns characteristic of the alleles/haplotypes of those patients at any locus. Then the direction of the disease associated gene from the locus can be determined. Specifically, by analyzing the degree of polymorphism associated with a particular trait at a given locus, the telomeric or centromeric direction of the location of the locus (locus-directional haplotyping) associated with the trait can be identified. That is, as the degree of polymorphism (the number of haplotypes) associated with the loci of individuals having the trait decreases, the locus is closer to the gene of interest. The locus associated with the trait will exhibit the highest degree of haplotype heterogeneity restriction. Conversely, as one moves further from the locus associated with a trait, the number of haplotypes of those with the trait increases until the gene associated with the trait is so far from the locus that those with the trait will have the same haplotypes as those without the trait for that locus.

In some cases, the next analyzed locus will not share patterns with the first-tested locus. When the haplotypic patterns at the next locus are not consistent with the previous locus patterns, either recombination has resulted in generation of a new haplotype involving alleles on both sides of the site of recombination and/or the border of the haplotypic region has been crossed. That is, the second locus is on the other side of a site of a recombination. This phenomenon is found most frequently around recombination hot spots. Such loci may be separated by the presence of another haplotypic region intermediate between two tested loci. A DNA sequence intermediate between the evaluated loci can then be analyzed to determine the borders of the haplotypic region or to locate each of the genetic loci associated with the haplotype.

Once the locations of the haplotypic region are established, the genetic loci within each border and, preferably, one central locus can be evaluated to determine the number of alleles at each locus and at the adjacent loci. This evaluation can determine the genetic variation patterns produced by the common alleles for each locus of a haplotypic region.

By evaluating the adjacent region of the chromosome in the same manner, the mapping method determines overlapping haplotypic regions (haplocontigs) in a selected region of a chromosome and can be used to establish the haplotypic regions throughout the genome.

In another aspect, the mapping method provides information regarding the degree of polymorphism associated with a genomic region of interest. By analyzing DNA from numerous individuals, the number of alleles and of haplotypes associated with a region of interest can be determined. PDLP and RFLP patterns produced in the analyses are more numerous and more closely linked to the genetic locus than RFLP sites located by classical methods, since the present method can effectively utilize all of the RFLP sites in the amplified DNA sequences. Allele/haplotype-specific amplification is the most preferred analysis method to quickly screen a locus. However, the method requires more sequence information prior to its implementation than PDLP or RFLP techniques.

Minimum sequencing enables sequence comparisons between genetically disparate individuals. In this way one can identify non-homologous regions and make rational selection of sites for restriction analysis or ASP HSP amplification. Then, additional individuals associated with particular patterns of variability in a population can be identified prior to sequencing. This analysis eliminates duplicative sequencing of individuals with the same haplotype. Prior to sequencing a genetic locus of interest, the allelic and sub-allelic haplotypic patterns associated with the locus are determined. Only one individual with a particular sub-allelic haplotypic pattern need be sequenced. However, preferably two or three individuals are sequenced to confirm that the selected sequence is representative of the haplotype rather than represents an individual variation. In this way, all the common alleles for a haplotypic region together with characteristic sub-allelic (haplotypic) groups can be identified and sequenced. Furthermore, individuals with relatively rare haplotypes, such as those associated with a rare genetic disease, can be recognized by direct evaluation of haplotypic patterns in individuals with the disease.

In particular, disease-associated alleles and haplotypes are revealed by restriction of the allele/haplotype heterogeneity in patients with a particular disease. That is, patients with a particular disease will have only a few of the alleles/ haplotypes which are present in the general population. For example, of the greater than 100 HLA haplotypes comprising alleles of the DRB/DQA/DQB loci, only about 30 of the haplotypes are associated with diabetes. Of those 30 haplotypes, only five or six haplotypes are associated with early onset disease in chinese and Caucasians.

Analysis of the individual variability for all genetic loci can identify previously unrecognized loci associated with monogenic disorders. The locus will be so tightly linked to the disease-associated gene that no recombination between the locus and the disease-associated gene will be observed. Further, the haplotypes associated with the disease will be restricted. That is, only a limited number of the haplotypes present in the normal population are also present in those patients with the disease.

Identification and analysis of genes associated with multigenic disorders can be performed in the same manner. Specifically, haplotypes associated with the disease will also be restricted in patients with the disease at each locus associated with the disease.

Location of Amplified DNA Sequence

Amplified DNA sequences containing from about 200 to 500 nt corresponding to intron sequences can be used to characterize the allele associated with the intervening sequence, particularly if the intervening sequence is adjacent to a variable exon of the locus. Furthermore, amplified DNA sequences containing from about 200 to 2,000 nt, preferably 400 to 500 nt, corresponding to non-coding sequences associated with genetic loci, preferably intervening sequences, reflect patterns subtypic of alleles which are characteristic of the haplotype. Therefore, amplified DNA sequences corresponding to non-coding sequences associated with genes, preferably introns, are produced to analyze the adjacent locus and remote locus alleles.

The amplified DNA sequence will necessarily be located in a region where there is sufficient sequence information to select primer sites. For disease-associated genes, frequently sequences for the region surrounding an RFLP site that correlates with the disease is known. Alternatively, the gene of interest may be known to be located near another genetic locus. In addition, if no further information is available, the STS sites characterized for the genome mapping project include sequence information for about 400 to 500 nucleotides and can be used.

When genomic DNA sequences are available, primers are located to produce an amplified DNA sequence corresponding to an intervening sequence. If the location of the variable exon(s) for a locus is known, the amplified DNA sequence is preferably located in an intron adjacent to the variable exon. More preferably, the amplified DNA sequence will span the variable exon and include a portion, preferably the majority, most preferably all, of both adjacent introns.

When only cDNA sequences are available and intron locations within the sequence are not identified, primers are selected at intervals of about 200 nt and used to amplify genomic DNA. If the amplified sequence contains about 200 nt, the location of the first primer is moved about 200 nt to one side of the second primer location and the amplification is repeated until either (1) an amplified DNA sequence that is larger than expected is produced or (2) no amplified DNA sequence is produced, indicating the presence of an intervening sequence that is too large for the amplification method. In either case, the location of an intron sequence has been determined.

When the primers span an intron and produce an amplified DNA sequence, the primers can be used on the DNA of numerous individuals to begin the analysis process. When no amplified DNA sequence is produced, the intron sequence defined by the primers may be too large. Either another intron sequence can be located, as described previously or anchored, one-sided amplification can be performed to produce a sequence corresponding to a portion of the intron. Those DNA sequences, or portions thereof, can be sequenced to locate a second primer site within the intron sequence to define an amplified DNA sequence for analysis.

The amplified DNA sequence is defined (by selection of the location of the primer sites) to contain mostly intron, rather than exon sequences, when the sequences of introns and exons (or the exon sequences and locations of exon-intron junctions) in the region to be amplified are known. Primer selection and preparation methods, as well as DNA amplification methods, are well known and are described in detail hereinafter.

Once an amplified DNA sequence containing intron sequences is produced, the primers are used to produce the corresponding amplified DNA sequences from a number of individuals. The sizes of the sequences and the fragment patterns using several restriction endonucleases can be examined to select an analytical method that demonstrates allelic and sub-allelic genetic diversity associated with the locus. Selection of endonucleases and production and analysis of RFLP patterns is well known and is described in detail hereinafter.

Once a primer pair or primer pair/endonuclease combination is selected, the DNA of about 100 individuals would be amplified and the lengths of the sequences (fragments) would be determined. The lengths of the sequences will fall into patterns related to the allele(s)/haplotype(s) of the individuals for that amplified sequence. For each chromosomal region, amplified sequences could be produced at various points along the region to determine each allele/haplotype associated with the region. An exemplary identification of the alleles/haplotypes found in one haplotypic region of the human genome is the identification of 35 of the known HLA haplotypes of the DRB/DQA/DQB loci. That analysis is described in detail in the examples. As will be readily apparent from the example, new patterns associated with rare haplotypes or haplotypes associated with other population groups can be readily identified by performing the analysis.

In a search for a gene associated with a genetic disease, there may be 30 to 40 haplotypes associated with the DNA region containing the gene. The sequence variation for those with the disease would be restricted to a relatively small number (3 to 8) of disease-associated haplotypes that would account for a substantial percentage (about 70%) of the disease population. Those haplotypes produce different patterns upon amplification and analysis. The DNA from a relatively small number of individuals with the disease, of the order of 20 to 100, can be quickly amplified, digested and analyzed. The patterns will fall into 3 to 8 groups, depending on the number of allelic variations of the locus. Only one representative sample of DNA from each allelic group need be sequenced. Preferably, two or three samples are sequenced to confirm the samples are representative. In this way, one can determine those individuals who have different haplotype-associated alleles prior to sequencing and avoid repeated sequencing of the most prevalent haplotypes.

For example, cystic fibrosis (CF) is an autosomal recessive disease, requiring the presence of a mutant gene on each chromosome. CF is the most common genetic disease in Caucasians, occurring once in 2,000 live births. It is estimated that one in forty Caucasians are carriers for the disease.

Recently a specific deletion of three consecutive basepairs in the open reading frame of the putative CF gene leading to the loss of a phenylalanine residue at position 508 of the predicted 1480 amino acid polypeptide was reported [Kerem et al, *Science* 245:1073–1080 (1989)]. Based on haplotype analysis, the deletion may account for most CF mutations in Northern European populations (about 68%). A second mutation is reportedly prevalent in some Southern European populations. Additional data indicate that several other mutations may cause the disease.

Studies of haplotypes of parents of CF patients (who necessarily have one normal and one disease-associated haplotype) indicated that there are at least 178 haplotypes associated with the CF locus. Of those haplotypes, 90 are associated only with the disease; 78 are found only in normals; and 10 are associated with both the disease and with normals (Kerem et al, supra). The disease apparently is caused by several different mutations, some in very low frequency in the population. As demonstrated by the haplotype information, there are more haplotypes associated with the locus than there are mutant alleles responsible for the disease.

The present method directly determines haplotypes associated with the locus and can detect haplotypes among the 178 currently recognized haplotypes associated with the disease-associated genetic locus. Additional haplotypes associated with the disease are readily determined through the rapid analysis of DNA of numerous CF patients by the methods of this invention. Furthermore, any mutations which may be associated with noncoding regulatory regions can also be detected by the method and will be identified by the screening process.

Rather than attempting to determine each defect in a coding region that causes the disease, the present method amplifies intron sequences associated with the locus to identify allelic and sub-allelic patterns. New PDLP and RFLP patterns produced by intron sequences indicate the presence of a previously unrecognized haplotype.

A detailed description of selection of primers, amplification methods, and analysis of DNA sequences is provided below. Those techniques can be used initially to determine the patterns produced by common alleles/haplotypes associated with the locus. Once the common patterns are established, the patterns can be refined so that additional haplotypes associated with a locus can be distinguished. This additional characterization allows new haplotypes to be more readily identified. This complete characterization is particularly valuable for loci associated with inherited diseases and for other medically important loci such as the HLA loci. However, for some loci, analysis of hundreds of individuals will demonstrate that there are only one or two haplotypes associated with the locus. Such small numbers indicate that a limited number of haplotypes are associated with the region. Analysis of another 100 individuals may provide an additional one or two haplotypes. DNA from numerous other individuals needs to be analyzed to detect haplotypes with a low frequency. Further characterization may not be desired for all such loci.

There are three major types of genetic variations that can be detected within an amplified DNA sequence and used to identify allelic and sub-allelic groups. Those variations, in order of ease of detection, are (1) a change in the length of the sequence, (2) a change in the presence or location of at least one restriction site and (3) the substitution of one or a few nucleotides that does not result in a change in a restriction site. Other variations within the amplified DNA sequence are also detectable. Alternatively, once sufficient sequence information about the locus has been developed, allele/haplotype-specific amplification can be performed to analyze DNA of numerous additional individuals for that locus. Allele/haplotype specific amplification is based on selection of primer sites that are characteristic of the allele/haplotype.

There are four types of techniques which can be used to detect the variations. The first is sequencing the amplified DNA sequence. Sequencing is the most time consuming and also the most revealing analytical method, since it detects any type of genetic variation in the amplified sequence. The second analytical method uses allele-specific oligonucleotides or sequence-specific oligonucleotides probes (ASO or SSO probes). Probes can detect single nucleotide changes which result in any of the types of genetic variations, so long as the exact sequence of the variable site is known.

A third type of analytical method detects sequences of different lengths (e.g., due to an insertion/deletion of nucleotides, to nucleotide substitutions that change the mobility or to a change in the location of a restriction site) and/or different numbers of sequences (due to either gain or loss of restriction sites). A preferred length difference detection method is by gel or capillary electrophoresis. To detect changes in the lengths of fragments or the number of fragments due to changes in restriction sites, the amplified sequence must be digested with an appropriate restriction endonuclease prior to analysis of fragment length patterns.

A fourth and most preferred type of analytical method is based on allele/haplotype-specific amplification to detect the presence of the selected allele/haplotype. In the fourth method, the locus-specific amplified DNA sequence is amplified with a nested primer pair specific for a selected allele/haplotype. Production of an amplified DNA sequence by the primer pair indicates the presence of the allele/haplotype. In a preferred embodiment of the method, each nested amplification is performed in a separate amplification reaction mixture so that the presence of an amplified DNA sequence indicates the presence of the allele/haplotype. Preferably, each primer pair produces an amplified DNA sequence of a different length and the lengths of the resultant amplified DNA sequences are determined to confirm the presence of the alleles/haplotypes.

Although the analytical techniques used to recognize allele-associated genetic variations in the amplified DNA sequence can include use of probes or sequencing of the amplified DNA sequence, those methods are preferably limited to particular applications, such as identification of an allele associated with a disease. For the most part, the initial analyses are based on the use of amplified DNA sequence and subsequent analysis based on either (1) the correlation of the length of the amplified DNA sequence with alleles/haplotypes, (1) the production of RFLP patterns that correlate with alleles/haplotypes or (3) sequence-specific amplification where the production of an amplified DNA sequence indicated the presence of a selected allele/haplotype. However, sequencing or use of probes may be the preferred analytical method for some genetic regions.

Primers

Selection of primer sites

The method of this invention is based on amplification of selected intron regions of genomic DNA. The methodology is facilitated by the use of primers that selectively hybridize to unique conserved regions of genomic DNA associated with a plurality of alleles of a genetic locus of interest and not other genetic loci.

Thus, the sites to which primers hybridize are selected in conserved regions in the area to be mapped. Conserved regions are determined on the basis of sequences from at least two individuals. If no further sequence information is available, conserved regions forming the restriction site, clone sequence STS site or any other marker used to delineate the region can be used.

When genomic DNA sequences are available, the primers are preferably located in conserved regions in the introns. When the only sequences available are cDNA sequences, the primers are located in conserved regions in the exons. If junctions of intron and exon sequences in the cDNA sequences are known, then the primer sites are preferably located near those junctions.

A locus-specific primer pair contains a 5' upstream primer that defines the 5' end of the amplified DNA sequence by hybridizing with the 5' end of the target sequence to be amplified and a 3' downstream primer that defines the 3' end of the amplified DNA sequence by hybridizing with the complement of the 3' end of the DNA sequence to be amplified. The primers in the primer pair do not hybridize with DNA of other genetic loci under the conditions used in the present invention.

For each primer of the locus-specific primer pair, the primer hybridizes to a plurality of alleles of the DNA locus to be amplified or to its complement. Preferably, the primer pair amplifies all alleles of the locus regardless of the associated haplotypes. However, primer pairs or combinations thereof that specifically bind with the most common alleles present in a particular population group or with groups of alleles that share a common sequence are also contemplated.

The amplified DNA sequence that is defined by the primers contains a sufficient number of non-coding region sequence nucleotides, preferably intron sequence nucleotides, to distinguish between alleles of an adjacent locus, and preferably, to identify the alleles of the locus which are present in the sample for all alleles of the locus, or all alleles of the group of alleles containing the selected sequences. In a most preferred embodiment, the primer-defined amplified DNA sequence contains a sufficient number of intron sequence nucleotides to distinguish between the haplotypes associated with the adjacent locus and one or more remote loci.

Length of sequence

The length of the amplified sequence which is required to include sufficient genetic variability to enable discrimination between all alleles/haplotypes of a locus bears a direct relation to the extent of the polymorphism of the locus (the number of alleles). That is, as the number of alleles and haplotypes associated with the tested locus increases, the size of an amplified sequence which contains sufficient genetic variations to distinguish each allele/haplotype increases. However, even for the HLA loci with numerous alleles and haplotypes, amplified DNA sequences of 2,000 nt are sufficient. Generally, amplified DNA sequences corresponding to 400 to 500 nt of intron sequence nucleotides from the intron adjacent to the variable exon are sufficient to distinguish all the haplotypes associated with the loci.

The ends of the amplified DNA sequence are defined by the primer pair used in the amplification. Conveniently, the primer pairs will hybridize with the DNA sequence of all alleles/haplotypes of the locus. Therefore, each primer sequence must correspond to a conserved region of the genomic DNA sequence. Thus, the location of the amplified sequence will, to some extent, be dictated by the need to locate the primers in conserved regions. When sufficient intron sequence information to determine conserved intron regions is not available, the primers can be located in conserved portions of the exons and used to amplify intron sequences between those exons.

When appropriately-located, conserved sequences are not unique to the genetic locus, a second primer pair located within the amplified sequence produced by the first primer pair can be used to provide an amplified DNA sequence specific for the genetic locus. At least one of the primers of the second primer pair is located in a conserved region of the amplified DNA sequence defined by the first primer pair. The second primer pair is used following amplification with the first primer pair to amplify a portion of the amplified DNA sequence produced by the first primer pair to produce a locus-specific amplified DNA sequence.

Considerations related to the genetic variation

The type of genetic variation to be detected in the amplified DNA sequence also influences the location and size of the sequence. As stated previously, the analyses are preferably based on allele/haplotype-specific amplification or on the presence of genetic variations that result in a change in the length of the amplified DNA sequence or a change in the presence or location of at least one restriction site.

For allele/haplotype-specific amplification, there are two considerations. The first is that the primer site for at least one of the nested primers is characteristic of an allele/haplotype. Those considerations are described in the discussion of nested primer specificity below. The second consideration is that preferably the amplified DNA sequence for each of the alleles/haplotypes differs in length. Consideration for selection of length differences are discussed below.

Genetic variations that result in a difference in the length of the primer-defined amplified DNA sequence, referred to herein as a primer-defined length polymorphism (PDLP), can be used to distinguish between alleles/sub-allelic groups of the genetic locus. The PDLPs result from insertions or deletions of relatively large stretches (in comparison to the total length of the amplified DNA sequence) of DNA in the portion of the intron sequence defined by the primer pair. To detect PDLPs, the amplified DNA sequence is located in a region containing insertions or deletions of a size that is detectable by the chosen method.

Alternatively, the length variation can be a perceived length variation which is due to a substitution of one or more nucleotides in the amplified DNA sequence that results in a change in electrophoretic mobility. This apparent length variation is referred to a primer-defined mobility variation (PDMP) and will be referred to herein as a type of PDLP. Such mobility differences are attributable to kinking or folding of the amplified DNA sequence due to particular combinations of nucleotides present in the sequence. Such combinations of nucleotides and the resultant mobility differences are well known. For example, regions rich in AT sequences tend to kink.

The amplified DNA sequence should have a length which provides optimal resolution of length differences. For electrophoresis, DNA sequences of about 300 to 500 bases in length provide optimal resolution of length differences. However, sequences as long as 800 to 1,000 nt are also readily distinguishable. Under appropriate conditions, either gel electrophoresis or capillary electrophoresis can detect as few as three nt differences in sequence lengths. Preferably the length differences will be at least 10, more preferably 20, most preferably 50 or more, nt between the alleles. Therefore, preferably, the amplified DNA sequence is between 300 to 1,000 nt and encompasses length differences of at least 3, preferably 10, most preferably 50 or more nt.

PDLPs can be produced in two general ways. In the first, the primers sites are located in a fixed position in the sample DNA sequence and the sequence between the primer sites varies depending on the alleles or haplotypes of the locus. In another embodiment, the primer sites are selected at varied positions to produce an amplified DNA sequence having a different length for each allele/haplotype of the locus, as described above for allele/haplotype-specific amplification.

When the variation to be detected is a change in a restriction site, the amplified DNA sequence necessarily contains at least one restriction site which (1) is present in one allele and not in another, (2) is apparently located in a different position in the sequence of at least two alleles, or (3) combinations thereof. The amplified sequence will preferably be located such that restriction endonuclease cleavage produces fragments of detectably different lengths, rather than two or more fragments of approximately the same length.

For the method described herein, it is contemplated that use of more than one amplified DNA sequence and/or use of more than one analytical method per amplified DNA sequence may be required for highly polymorphic loci, loci where alleles differ by single nucleotide substitutions that are not unique to the allele, or when information regarding remote locus alleles (haplotypes) is desired. More particularly, it may be necessary to combine a PDLP analysis with an RFLP analysis, to use two or more amplified DNA sequences located in different positions, to perform multiple nested amplifications on the amplified DNA sequence produced by a prior nested amplification, or to digest one amplified DNA sequence with a plurality of endonucleases to provide distinctive allelic and sub-allelic patterns for a locus. These combinations are intended to be included within the scope of this invention.

Length and sequence homology of primers

Each locus-specific primer includes a number of nucleotides which, under the conditions used in the hybridization, are sufficient to hybridize with alleles of the locus to be amplified and to be free from hybridization with alleles of other loci. The specificity of the primer increases with the number of nucleotides in its sequence under conditions that provide the same stringency. Therefore, longer primers are desirable. Sequences with fewer than 15 nucleotides are less certain to be specific for a particular locus. That is, sequences with fewer than 15 nucleotides are more likely to be present in a portion of the DNA associated with other genetic loci, particularly loci of other common origin or evolutionarily closely related origin, in inverse proportion to the length of the nucleotide sequence.

Each primer preferably includes at least about 15 nucleotides, more preferably at least about 20 nucleotides. The primer preferably does not exceed about 30 nucleotides, more preferably about 25 nucleotides. Most preferably, the primers have between about 20 and about 25 nucleotides.

When two sets of primer pairs are used sequentially, with the second primer pair amplifying the product of the first primer pair, the primers can be the same size as those used for the first amplification. However, smaller primers can be used in the second amplification and provide the requisite specificity. The primers of the second primer pair can have 15 or fewer nucleotides. When two sets of primer pairs are used to produce two amplified sequences, the second amplified DNA sequence is used in the subsequent analysis of genetic variation and must meet the requirements discussed previously for the amplified DNA sequence.

The primers preferably have a nucleotide sequence that is identical to a portion of the DNA sequence to be amplified or its complement. However, a primer having two of the first five nucleotides of the 3' end of the primer that differ from the target DNA sequence or its complement also can be used. Any nucleotides that are not identical to the sequence or its complement are not the 3' nucleotide of the primer. The 3' end of the primer preferably has at least two, preferably three or more, nucleotides that are complementary to the sequence to which the primer binds. Any nucleotides at the 3' end that are not identical to the sequence to be amplified or its complement will preferably not be adjacent in the primer sequence. More preferably, noncomplementary nucleotides in the primer sequence will be separated by at least two, more preferably at least three, nucleotides. The primers should have a melting temperature ($T_m$) from about 55° to 75° C. Preferably the $T_m$ is from about 60° C. to about 65° C. to facilitate stringent amplification conditions. The degree of homology, length, $T_m$ and other considerations for primer selection to ensure specific hybridization are well known and do not constitute part of the invention.

The primers can be prepared using a number of methods, such as, for example, the phosphotriester and phosphodiester methods or automated embodiments thereof. The phosphodiester and phosphotriester methods are described in Cruthers, *Science* 230:281–285 (1985); Brown et al, *Meth. Enzymol.,* 68:109 (1979); and Nrang et al, *Meth. Enzymol.,* 68:90 (1979). In one automated method, diethylphosphoramidites which can be synthesized as described by Beaucage et al, *Tetrahedron letters,* 22:1859–1962 (1981) are used as starting materials. A method for synthesizing primer oligonucleotide sequences on a modified solid support is described in U.S. Pat. No. 4,458,066. Each of the above references is incorporated herein by reference in its entirety.

Amplification

Once a primer pair is selected, genomic DNA is amplified to produce an amplified DNA sequence. The conditions and reagents for DNA amplification are well known. A preferred amplification method is the polymerase chain reaction (PCR). PCR amplification methods are described in U.S. Pat. No. 4,683,195 (to Mullis et al, issued Jul. 28, 1987); U.S. Pat. No. 4,683,194 (to Saiki et al, issued Jul. 28, 1987); Saiki et al, *Science,* 230:1350–1354 (1985); Scharf et al, *Science,* 324:163–166 (1986); Kogan et al, *New Engl. J. Med,* 317:985–990 (1987) and Saiki, Gyllensten and Erlich, *The Polymerase Chain Reaction in Genome Analysis: A Practical Approach,* ed. Davies pp. 141–152, (1988) I.R.L. Press, Oxford. Each of the above references is incorporated herein by reference in its entirety. Although the remaining description is based on use of PCR amplification methods, other DNA amplification methods such as the NASBA method (Compton *Nature* 350:91 [1991]) can also be used. Adaptation of another DNA amplification method to this analysis method is within the level of skill in the art.

Prior to amplification, a sample of genomic DNA is obtained. All nucleated cells contain genomic DNA and, therefore, are potential sources of the required DNA. For higher animals, peripheral blood cells are typically used rather than tissue samples. As little as 0.01 to 0.05 cc of peripheral blood provides sufficient DNA for amplification. Hair, semen and tissue can also be used as samples. Genomic DNA libraries are available and are readily constructed by well known methods.

DNA isolation from nucleated cells is described by Kan et al, *N. Engl. J. Med.* 297:1080–1084 (1977); Kan et al, *Nature* 251:392–392 (1974); and Kan et al, *PNAS* 75:5631–5635 (1978). Each of the above references is incorporated herein by reference in its entirety. Extraction procedures for samples such as blood, semen, hair follicles, semen, mucous membrane epithelium and other sources of genomic DNA are well known. For plant cells, digestion of the cells with cellulase releases DNA. Thereafter, the DNA is purified as described above.

The extracted DNA can be purified by dialysis, chromatography, or other known methods for purifying polynucleotides prior to amplification. Typically, the DNA is not purified prior to amplification.

The amplified DNA sequence is produced by using the portion of the DNA and its complement bounded by the primer pair as a template. As a first step in the method, the DNA strands are separated into single stranded DNA. This strand separation can be accomplished by a number of methods including physical or chemical means. A preferred method is the physical method of separating the strands by heating the DNA until it is substantially (approximately 93%) denatured. Heat denaturation involves temperatures ranging from about 80° to 105° C. for times ranging from about 15 to 30 seconds. Typically, heating the DNA to a temperature of from 90° to 93° C for about 30 seconds to 1 minute is sufficient.

The primer extension product(s) produced are complementary to the primer-defined region of the DNA and hybridize therewith to form a duplex of equal length strands. The duplexes of the extension products and their templates are then separated into single-stranded DNA. When the complementary strands of the duplexes are separated, the strands are ready to be used as a template for the next cycle of synthesis of additional DNA strands.

Each of the synthesis steps can be performed using conditions suitable for DNA amplification. Generally, the amplification step is performed in a buffered aqueous solution, preferably at a pH of about 7 to about 9, more preferably about pH 8. A suitable amplification buffer contains Tris-HCl as a buffering agent in the range of about 10 to 100 mM. The buffer also includes a monovalent salt, preferably at a concentration of at least about 10 mM and not greater than about 60 mM. Preferred monovalent salts are KCl, NaCl and $(NH_4)_2SO_4$. The buffer also contains $MgCl_2$ at about 5 to 50 mM. Other buffering systems such as hepes or glycine-NaOH and potassium phosphate buffers can be used. Typically, the total volume of the amplification reaction mixture is about 50 to 100 $\mu$l.

Preferably, for genomic DNA, a molar excess of about $10^6$:1 primer:template of the primer pair is added to the buffer containing the separated DNA template strands. A large molar excess of the primers improves the efficiency of the amplification process. In general, about 100 to 150 ng of each primer is added.

The deoxyribonucleotide triphosphates dATP, dCTP, dGTP and dTTP are also added to the amplification mixture in amounts sufficient to produce the amplified DNA sequences. Preferably, the dNTPs are present at a concentration of about 0.75 to about 4.0 mM, more preferably about 2.0 mM. The resulting solution is heated to about 90° to 93° C for from about 30 seconds to 1 minute to separate the strands of the DNA. After this heating period the solution is cooled to the amplification temperature.

Following separation of the DNA strands, the primers are allowed to anneal to the strands. The annealing temperature varies with the length and GC content of the primers. Those variables are reflected in the $T_m$ of each primer. The extension reaction step is performed following annealing of the primers to the genomic DNA.

An appropriate agent for inducing or catalyzing the primer extension reaction is added to the amplification mixture either before or after the strand separation (denaturation) step, depending on the stability of the agent under the denaturation conditions. The DNA synthesis reaction is allowed to occur under conditions which are well known in the art. This synthesis reaction (primer extension) can occur at from room temperature up to a temperature above which the polymerase no longer functions efficiently. Elevating the amplification temperature enhances the stringency of the reaction. As stated previously, stringent conditions are necessary to ensure that the amplified sequence and the DNA template sequence contain the same nucleotide sequence, since substitution of nucleotides can alter the restriction sites or probe binding sites in the amplified sequence.

The inducing agent may be any compound or system which facilitates synthesis of primer extension products, preferably enzymes. Suitable enzymes for this purpose include DNA polymerases (such as, for example, E. coli DNA polymerase I, Klenow fragment of E. coli DNA polymerase I, T4 DNA polymerase), reverse transcriptase, and other enzymes (including heat-stable polymerases), which facilitate combination of the nucleotides in the proper manner to form the primer extension products. Most preferred is Taq polymerase or other heat-stable polymerases which facilitate DNA synthesis at elevated temperatures (about 60° to 90° C.). Taq polymerase is described, e.g., by Chien et al, J. Bacteriol., 127:1550–1557 (1976). That article is incorporated herein by reference in its entirety. When the extension step is performed at about 72° C, about 1 minute is required for every 1,000 bases of target DNA to be amplified.

The synthesis of the amplified sequence is initiated at the 3' end of each primer and proceeds toward the 5' end of the template along the template DNA strand, until synthesis terminates, producing DNA sequences of different lengths. The newly synthesized strand and its complementary strand form a double-stranded molecule which is used in the succeeding steps of the process. In the next step, the strands of the double-stranded molecule are separated (denatured) as described above to provide single-stranded molecules.

New DNA is synthesized on the single-stranded template molecules. Additional polymerase, nucleotides and primers can be added if necessary for the reaction to proceed under the conditions described above. After this step, half of the extension product consists of the amplified sequence bounded by the two primers. The steps of strand separation and extension product synthesis can be repeated as many times as needed to produce the desired quantity of the amplified DNA sequence. The amount of the amplified sequence produced accumulates exponentially. Typically, about 25 to 30 cycles are sufficient to produce a suitable amount of the amplified DNA sequence for analysis.

The amplification method can be performed in a step-wise fashion where after each step new reagents are added, or simultaneously, where all reagents are added at the initial step, or partially step-wise and partially simultaneously, where fresh reagent is added after a given number of steps. The amplification reaction mixture can contain, in addition to the sample genomic DNA, the four nucleotides, the primer pair in molar excess, and the inducing agent, e.g., Taq polymerase.

Each step of the process occurs sequentially notwithstanding the initial presence of all the reagents. Additional materials may be added as necessary. Typically, the polymerase is not replenished when using a heat-stable polymerase. After the appropriate number of cycles to produce the desired amount of the amplified sequence, the reaction may be halted by inactivating the enzymes or separating the components of the reaction or stopping thermal cycling.

In a preferred embodiment of the method, the amplification includes the use of a second primer pair to perform a second amplification following the first amplification. The second primer pair defines a DNA sequence which is a portion of the first amplified sequence. That is, at least one of the primers of the second primer pair defines one end of the second amplified sequence which is within the ends of the first amplified sequence. In this way, the use of the second primer pair helps to ensure that any amplified sequence produced in the second amplification reaction is specific for the tested locus. That is, non-target sequences which may be copied by a locus-specific pair are unlikely to contain sequences that hybridize with a second locus-specific primer pair located within the first amplified sequence.

Analysis of the Amplified DNA Sequence

As discussed previously, the method used to analyze the amplified DNA sequence to characterize the allele(s) present in the sample DNA depends on the genetic variation in the sequence. When distinctions between alleles include primer-defined length polymorphisms, the amplified sequences are separated based on length, preferably using gel or capillary electrophoresis. When the analysis is based on RFLP fragment patterns, the amplified sequences are digested with one or more restriction endonucleases to produce a digest and the resultant fragments are separated based on length, preferably using gel or capillary electrophoresis. A most preferred method is an amplification-specific method in which the presence of a nested amplified DNA sequence indicates the presence of a selected an allele or haplotype.

Each step of the various analytical methods uses procedures such as DNA amplification, endonuclease digestion and gel electrophoresis that are well known and are described below.

Allele-or Haplotype-Specific Amplification Analysis

Allele- or haplotype-specific amplification is a preferred analysis method which can be performed once 400 to 500 bp of sequence information for the region for about 15 to 20 individuals of the most diverse ethnic groups possible region is available.

As a first step in the analysis method, a locus-specific amplified DNA sequence is prepared for use as a target DNA sequence for amplification by a nested sequence-specific primer pair, allele-specific primer pair or haplotype-specific primer pair. The target DNA sequence preferably corresponds to a portion of the genetic locus including a variable exon or exons just downstream from the variable exon and adjacent intron sequence nucleotides. The method is based on amplification of the target DNA sequence using a primer pair wherein at least one of the primers of the pair hybridizes to the target DNA sequence only when a selected sequence is present in the target sequence. As stated previously, the sequence polymorphism can be characteristic of one allele or a group of alleles of the genetic locus. Alternatively, the sequence polymorphism can be a sub-allelic variation characteristic of a haplotype associated with the genetic locus and one or more adjacent loci. In this way, production of an amplified DNA sequence indicates that the selected sequence polymorphism, and thus the selected sub-allelic variation, allele or group of alleles, is present in the target DNA.

In one embodiment, the first amplification uses a locus-specific primer pair which produces a target DNA sequence irrespective of the alleles or haplotypes present in the sample. In another embodiment, the locus-specific primer pair produces a target DNA sequence only when a selected group of alleles having a common sequence polymorphism is present in the sample. The subsequent amplification of the target sequence is performed using primers for alleles in the group.

The second amplification preferably contains primer pairs for sufficient sequence polymorphisms to determine the alleles/haplotypes in the sample. In one embodiment, a plurality of amplifications are performed wherein each amplification reaction mixture contains a single primer pair. Detection of the presence of amplification in a reaction mixture determines that the allele for which the primer pair is specific is present in the sample. In another embodiment, multiple DNA amplifications are performed in a single reaction mixture using pairs of primers wherein each primer pair in the reaction mixture produces an amplified DNA sequence having a distinguishable length from the sequence produced by every other primer pair in the reaction mixture. Determination of the length of the resultant amplified DNA sequence(s) identifies the sequence polymorphism(s) present in the target DNA. In a preferred embodiment, sufficient combinations of primer pairs are used so that the resultant amplified DNA sequences determine both alleles of the genetic locus present in the sample.

Nested Primer Pairs

This method is based on amplification of a target DNA sequence using a nested primer pair wherein the presence of amplification by the nested primer pair indicates that a particular sequence polymorphism is present in the sample. The sequence polymorphism can be characteristic of one allele, a group of alleles of the genetic locus or a sub-allelic variation characteristic of one or more individuals or characteristic of a haplotype associated with the genetic locus and one or more adjacent loci.

In one preferred embodiment, the target DNA sequence is an amplified DNA sequence produced by a locus-specific primer pair that amplifies sample genomic DNA irrespective of the alleles or haplotypes present in the sample. In another preferred embodiment, the target DNA sequence encompasses groups of alleles of the locus, but not all of the alleles.

To effect allele-specific or haplotype-specific amplification, at least one primer in each nested primer pair is selected so that the primer hybridizes to the DNA sequence only when the selected sequence polymorphism is present. In this way, the presence of an amplified DNA sequence indicates that the sequence polymorphism is present in the sample. This is in contrast to most prior art DNA amplification methods wherein primers bind to a conserved region and the resultant amplified DNA sequence is analyzed, usually by use of oligoprobes, for the presence of the polymorphism in the amplified sequence.

At least one primer of each primer pair selectively hybridizes with a sequence polymorphism that is characteristic of (1) a multiplicity of alleles of a genetic locus but is not present in all of the alleles of the locus (a sequence-specific primer or SSP), (2) one allele of a genetic locus (an allele-specific primer or ASP), (3) one haplotype associated with a genetic locus and one or more adjacent loci (a haplotype-specific primer or HSP) or (4) a particular individual or group of individuals (an individual-specific primer or ISP). The other primer of the primer pair can be less specific, as discussed above.

Each of the nested amplified DNA sequences are located with the target DNA sequence. The location of each of the nested amplified DNA sequence within the target DNA is selected so that one or both of the ends of the amplified DNA sequence include a sequence polymorphism of the desired specificity. That is, either the 3' end or the 5' end, or both ends, of the amplified DNA sequence contain a sequence polymorphism to which either a sequence-specific, allele-specific, haplotype-specific or individual-specific primer hybridizes.

Preferably, the primers are also located such that each primer pair of in a reaction mixture defines an amplified DNA sequence of a different length. More preferably, the primers are located such that each nested primer pair associated with the genetic locus defines an amplified DNA sequence of a different length.

The amplified DNA sequence produced by the nested primers can vary in length from about 50 to 700 bp, preferably from 50 to 300 bp, more preferably from 50 to 100 bp. Each of the nested amplified DNA sequences preferably also differs from each other nested amplified DNA sequence in the reaction mixture, preferably each nested amplified DNA sequence for the locus, by at least a sufficient number of nucleotides so that the amplified DNA sequences can be readily distinguished by gel electrophoresis.

The length differences can be due to a difference in the number of nucleotides in the sequence (a primer-defined length polymorphism or PDLP) or can be an apparent length difference due to differences in mobility of the sequence on a gel (a primer-defined mobility polymorphism or PDMP). A description of gel electrophoretic analysis of PDLPs or PDMPs is described in detail hereinafter.

The considerations for specific hybridization of nested primers for the second amplification differ somewhat from the conditions required for locus-specific amplification since the primers need only be sufficiently specific for purposes of amplifying a selected DNA sequence, the target sequence produced in the first amplification. The differences in the consideration for nested primers are well known. For the nested primers, each primer can vary in length from about 10 to about 30, preferably from 15 to about 20 nt in length, most preferably about 18 nt in length. For each specific primer of the primer pair (an SSP, ASP, HSP, or ISP), the 3' end of the primer is selected to hybridize to a unique region of the target sequence which is characteristic of the sequence, allele haplotype or individual variation to be detected.

One unique nucleotide at the 3' end is sufficient to ensure specificity under conditions that provide an appropriate degree of stringency for the amplification reaction. When possible, a location having two or three unique nucleotides at the 3' end of the primer site can be used. The primer and the primer site must be complementary for at least the 3' nucleotide of the primer. In addition to the 3' nucleotide, preferably at least two of the adjacent four nucleotides, more preferably five nucleotides at the 3' end of the primer are also complementary to the primer site sequence. Preferably, at least three nucleotides, more preferably five nucleotides, at the 5' end of the primer, are also complementary to the primer site sequence. A non-complementary region near the center of the primer, preferably where any non-complementary nucleotides are not adjacent, provides sufficient homology for specific amplification.

The Analysis Method

As described hereinbefore, the analysis method involves a first amplification with locus-specific primers to produce a target DNA sequence. The target DNA sequence is amplified with nested primer pairs specific for portions of the target sequence characteristic of the sequence, allele, haplotype or individual variation to be detected. The method can be performed in a number of different ways and is characterized by the presence of an amplified DNA sequence produced by a nested primer pair indicating that a sequence for which the pair is specific is present in the sample.

The reagents and conditions used for DNA amplification do not differ from those of the locus-specific amplification. The following description of the method is written in terms of detecting alleles of the locus for purposes of clarity. The same considerations are involved in detecting sub-allelic variations.

First amplification

The first step of the analysis method is amplification of genomic DNA with locus-specific primers to produce a locus-specific amplified DNA sequence. As stated previously, the locus-specific primers produce an amplified DNA sequence for a group of alleles of the - locus having a common sequence polymorphism. The first amplification can be performed in one of two ways.

In one embodiment, the locus-specific primer pair produces an amplified DNA sequence irrespective of the alleles present in the sample genomic DNA. The resultant locus-specific amplified DNA sequence is used as the target DNA for the subsequent method steps.

In another preferred embodiment, a locus specific primer pair amplifies a plurality of alleles of the locus, but not all alleles of the locus. Use of this embodiment means that a plurality of locus-specific primer pairs are required to amplify all the alleles of the locus. However, the second amplification need only be by primers specific for the group of alleles having the sequence polymorphism of the locus-specific primer pair that produces the target DNA sequence. This method can result in a smaller number of total DNA amplifications being required to analyze a particular sample.

Each of the locus-specific primer pairs can be present in a separate amplification reaction mixture. In that case, the presence of an amplified DNA sequence indicates the groups of the alleles in the sample. Alternatively, two or more locus-specific primer pairs can be present in a single amplification reaction mixture. In that case, each of the resultant amplified DNA sequences is of a distinguishable length and is electrophoresed to determine the group of alleles present in the sample. The technique of combining multiple primer pairs in a single reaction mixture is referred to as multiplexing. Considerations involved in multiplexing are described in detail below in the discussion of the second amplification.

Second amplification

The second amplification is performed using primer pairs that amplify a DNA sequence within the target DNA. In the second amplification, the primers produce amplified DNA sequences indicative of the primer pair used responsible for the amplification. That is, at least one primer of the primer pair hybridizes to a DNA sequence characteristic of an allele or group of alleles of the locus. Production of an amplified DNA sequence by a particular primer pair or group of primer pairs indicates that the allele is present in the sample.

When the target sequence encompasses all alleles of the locus, an amplification for each allele is performed. In one embodiment, a separate reaction mixture is prepared for a primer pair characteristic of each allele of the locus. Determining the one or two reaction mixtures that produced an amplified DNA sequence identifies the allele(s) present in the sample. In a preferred embodiment, each amplified DNA sequence differs in length and the length of the resultant amplified DNA sequences are determined to confirm the alleles present in the sample.

Alternatively, at least one of the second reaction mixtures can contain two or more primer pairs. By selecting combinations of primer pairs for a reaction mixture so that each primer pair produces an amplified DNA sequence having a distinguishable length from the amplified DNA sequences produced by every other primer pair in the reaction mixture, the primer pair responsible for production of the amplified DNA sequence can be readily identified by determining the length of the amplified DNA sequence. Thus the sequence polymorphism present in the target DNA can be readily identified by the determining the length of the amplified DNA sequence.

When a plurality of primer pairs are to be used in a single reaction mixture, the primers of each pair are selected so that the length of the amplified DNA sequence is distinguishable from the lengths of all other amplified DNA sequences produced by other primer pairs present in the reaction mixture. Each primer of the pair can be specific for the selected allele. Alternatively, two or more primer pairs in the reaction mixture can share a common primer. When one primer pair in a reaction mixture utilizes a common primer, conveniently, all the primer pairs in the reaction mixture utilize the common primer. In that case, the allele-specific primer for each of the primer pairs will be selected at locations that are sufficiently far from the other allele-specific primers to be distinguishable by gel electrophoresis.

In a preferred embodiment, only one amplified DNA sequence is produced for each allele. That is, preferably, there is one allele-specific primer pair for each allele of the locus. For example, when several allele-specific primer pairs are used, the primers for each pair are selected so that only one amplified DNA sequence is produced when the allele is present in the target DNA. However, patterns of sequence-specific amplified DNA sequences which are characteristic of an allele when occurring together are also contemplated.

In another embodiment, one or more of the nested primer pairs in the second reaction mixture are sequence-specific primers and amplify a group of alleles of the locus. An additional amplification using nested primers to amplify the amplified DNA sequence produced by second amplification is used to determine the alleles within the second amplified DNA sequence.

The analysis method described above for alleles of the locus can be readily applied by one of ordinary skill in the art to analysis of suballelic polymorphisms, particularly haplotypic polymorphisms, or to use of groups of sequence-specific primer that produce patterns of amplified DNA sequences that characterize the alleles/haplotypes or that are amplified with nested primers to determine the alleles/haplotypes.

Production of RFLP Fragment Patterns
Restriction endonucleases

A restriction endonuclease is an enzyme that cleaves or cuts DNA hydrolytically at a specific nucleotide sequence called a restriction site. Endonucleases that produce blunt end DNA fragments (hydrolysis of the phosphodiester bonds on both DNA strands occur at the same site) as well as endonucleases that produce sticky ended fragments (the hydrolysis sites on the strands are separated by a few nucleotides from each other) can be used.

Restriction enzymes are available commercially from a number of sources including Sigma Pharmaceuticals, Bethesda Research Labs, Boehringer-Manheim and Pharmacia. As stated previously, a restriction endonuclease used in the present invention cleaves an amplified DNA sequence of this invention to produce a digest comprising a set of fragments having distinctive fragment lengths. In particular, the fragments for one allele/haplotype of a locus differ in size from the fragments for other alleles/haplotypes of the locus. The patterns produced by separation and visualization of the fragments of a plurality of digests are sufficient to distinguish allelic and sub-allelic patterns for the locus. More particularly, the endonucleases are chosen so that by using one or more digests of the amplified sequence, the alleles of a locus can be distinguished.

In selecting an endonuclease, the important consideration is the number of fragments produced for amplified sequences of the various alleles of a locus. More particularly, a sufficient number of fragments must be produced to distinguish between the alleles haplotypes. However, the number of fragments must not be so large or so similar in size that a pattern that is not distinguishable from those of other haplotypes by the particular detection method is produced. This selection is preferably performed by analyzing representative sequences and determining useful restriction endonucleases for the sequence rather than by empirically combining different endonucleases with the amplified DNA sequences and evaluating the sufficiency of the resultant patterns.

One of ordinary skill can readily determine whether an endonuclease produces RFLP fragments having distinctive fragment lengths. The determination can be made experimentally by cleaving an amplified sequence for each allele with the designated endonuclease in the invention method. The fragment patterns can then be analyzed. Preferably, the sequences are analyzed and an endonuclease restriction sites present in the sequences of the locus that produce fragments characteristic of alleles/haplotypes are selected. Distinguishable patterns will be readily recognized by determining whether comparison of two or more digest patterns is sufficient to detect differences between the patterns of the alleles. Such comparisons can be made by producing the fragments and separating the fragments on a gel. Alternatively, the fragments produced by an endonuclease can be determined by analyzing known sequences to determine the lengths of the fragments.

Production of RFLP fragments

Following amplification, the amplified DNA sequence is combined with an endonuclease that cleaves or cuts the amplified DNA sequence hydrolytically at a specific restriction site. The combination of the endonuclease with the amplified DNA sequence produces a digest containing a set of fragments having distinctive fragment lengths. U.S. Pat. No. 4,582,788 (to Erlich, issued Apr. 15, 1986) describes an HLA typing method based on restriction length polymorphism (RFLP). That patent is incorporated herein by reference in its entirety.

In a preferred embodiment, two or more aliquots of the amplification reaction mixture having approximately equal amounts of DNA per aliquot are prepared. Conveniently about 5 to about 10 $\mu l$ of a 100 $\mu l$ reaction mixture is used for each aliquot. Each aliquot is combined with a different endonuclease to produce a plurality of digests. In this way, by using a number of endonucleases for a particular amplified DNA sequence, locus-specific combinations of endonucleases that distinguish a plurality of alleles of a particular locus can be readily determined. Following preparation of the digests, each of the digests can be used to form RFLP patterns. Preferably, two or more digests can be pooled prior to pattern formation.

Alternatively, two or more restriction endonucleases can be used to produce a single digest. The digest differs from one where each enzyme is used separately and the resultant fragments are pooled since fragments produced by one enzyme may include one or more restriction sites recognized by another enzyme in the digest. Patterns produced by simultaneous digestion by two or more enzymes will include more fragments than pooled products of separate digestions using those enzymes and will be more complex to analyze.

The digestion of the amplified DNA sequence with the endonuclease can be carried out in an aqueous solution under conditions favoring endonuclease activity. Typically the solution is buffered to a pH of about 6.5 to 8.0. Mild temperatures, preferably about 20° C. to about 45° C., more preferably physiological temperatures (25° to 40° C.), are employed. Restriction endonucleases normally require magnesium ions and, in some instances, cofactors (ATP and S-adenosyl methionine) or other agents for their activity. Therefore, a source of such ions, for instance inorganic magnesium salts, and other agents, when required, are present in the digestion mixture. Suitable conditions are described by the manufacturer of the endonuclease and generally vary as to whether the endonuclease requires high, medium or low salt conditions for optimal activity.

The amount of DNA in the digestion mixture is typically in the range of 1% to 20% by weight. In most instances 5 to 20 µg of total DNA digested to completion provides an adequate sample for production of RFLP fragments. Excess endonuclease, preferably one to five units/µg DNA, is used.

The set of fragments in the digest is preferably further processed to produce RFLP patterns which are analyzed. If desired, the digest can be purified by precipitation and resuspension as described by Kan et al, *PNAS* 75:5631–5635 (1978), prior to additional processing. That article is incorporated herein by reference in its entirety.

Once produced, the fragments are analyzed by well known methods. Preferably, the fragments are analyzed using electrophoresis. Gel electrophoresis methods are described in detail hereinafter. Capillary electrophoresis methods can be automated (as by using Model 207A analytical capillary electrophoresis system from Applied Biosystems of Foster City, Calif.) and are described in Chin et al, *American Biotechnology Laboratory News Edition*, December, 1989.

Electrophoretic Separation of DNA Fragments

Electrophoresis is the separation of DNA sequence fragments contained in a supporting medium by size and charge under the influence of an applied electric field. Gel sheets or slabs, e.g. agarose, agarose-acrylamide or polyacrylamide, are typically used for analysis of nucleotide sequencing. The electrophoresis conditions effect the desired degree of resolution of the fragments. A degree of resolution that separates fragments that differ in size from one another by as little as 10 nucleotides is usually sufficient. Preferably, the gels will be capable of resolving fragments which differ by 3 to 5 nucleotides. However, for some purposes, discrimination of sequence differences of at least 100 nt may be sufficient for the analysis.

Preparation and staining of analytical gels is well known. For example, a 3% Nusieve 1% agarose gel which is stained using ethidium bromide is described in Boerwinkle et al, *PNAS*, 86:212–216 (1989). Detection of DNA in polyacrylamide gels using silver stain is described in Goldman et al, *Electrophoresis*, 3:24–26 (1982); Marshall, *Electrophoresis*, 4:269–272 (1983); Tegelstrom, *Electrophoresis*, 7:226–229 (1987); and Allen et al, *BioTechniques* 7:736–744 (1989). The method described by Allen et al, using large-pore size ultrathin-layer, rehydratable polyacrylamide gels stained with silver is preferred. Each of those articles is incorporated herein by reference in its entirety.

This invention is further illustrated by the following specific but non-limiting examples. Temperatures are given in degrees Centigrade and concentrations as weight percentages unless otherwise specified. Procedures that are constructively reduced to practice are described in the present tense, and procedures that have been carried out in the laboratory are set forth in the past tense.

EXAMPLE 1

Analysis of the HLA DQA Locus

The haplotypes of the HLA DQA1 locus were analyzed as described below. DNA from individuals of each known haplotype of the DQA1 locus was evaluated. Approximately 1 µg of sample DNA was combined in a total volume of 100 µl with a primer pair (1 µg of each primer), dNTPs (2.5 mM each) and 2.5 units of Taq polymerase in amplification buffer (50 mM KCl; 10 mM Tris-HCl, pH 8.0; 2.5 mM MgCl$_2$; 100 µg/ml gelatin) to form amplification reaction mixtures.

The sequences of the primers were:

SGD 001—5' TTCTGAGCCAGTCCTGAGA 3'(SEQ ID NO: 1); and

SGD 003—5' GATCTGGGGACCTCTTGG 3'(SEQ ID NO: 2).

These primers hybridize to sequences about 500 bp upstream from the 5' end of the second exon and 50 bp downstream from the second exon and produce amplified DNA sequences in the 700 to 800 bp range. Each primer was synthesized using an Applied Biosystems model 308A DNA synthesizer.

The amplification procedure used thirty cycles of 94° C. for 30 seconds, 60° C. for 30 seconds, and 72° C. for 60 seconds. Following amplification, the amplified DNA sequences were electrophoresed on a 4% polyacrylamide gel to determine the PDLP type. In this case, amplified DNA sequences for the eight alleles produced five different length PDLP sequences, (demonstrating the presence of at least 5 haplotypes). Subsequent enzyme digestion used to produce RFLP patterns distinguished additional allelic and sub-allelic (haplotypic) patterns.

The amplified DNA sequences were aliquoted and separately digested using the restriction enzymes AluI, DdeI and MboII (Bethesda Research Laboratories). The digestion was performed by mixing 5 units (1 µl) of enzyme with 10 µl of the amplified DNA sequence (between about 0.5 and 1 µg of DNA) in the enzyme buffer provided by the manufacturer according to the manufacturer's directions to form a digest. The digest was then incubated for 2 hours at 37° C. for complete enzymatic digestion.

The products of the digestion reaction were mixed with approximately 0.1 µg of "ladder" nucleotide sequences (nucleotide control sequences beginning at 123 bp in length and increasing in length by 123 bp to a final size of about 5,000 bp; available commercially from Bethesda Research Laboratories, Bethesda Md.) and electrophoresed using a 4% horizontal ultra-thin polyacrylamide gel (E-C Apparatus, Clearwater Fla.). The bands in the gel were visualized (stained) using silver stain technique [Allen et al, *BioTechniques* 7:736–744 (1989)].

PDLP groups and fragment patterns for each of the DQA1 haplotypes with each of the three endonucleases are illustrated in Table 1.

| | | | AluI | | | | | | | | | |
|---|---|---|---|---|---|---|---|---|---|---|---|---|
| PDLP | DR | Dw | 480/410 | 405/400 | 390/370 | 360/350 | 340/330 | 310/300 | 270/240 | 120/110 | 100 |
| 0101 | 1 | 1 |  |  |  |  |  | + | + | + |  |
|  | 1 | 20 |  |  |  |  |  | + | + | + |  |
|  | 14 | 9 |  |  |  |  |  | + | + | + |  |
| 0102 | 15 | 2 | + |  |  | + | + |  | + |  |  |
|  | 16 | 21 | +| |  |  |  | + | + |  | + |  |  |
|  | 13 | 19 | + |  |  |  | + | + |  | + |  |  |
| 0103 | 13 | 18,24 |  |  |  |  |  | + | + | + |  |
|  | 13 | 18,25 |  |  |  |  |  | + | + | + |  |
|  | 8 | 8.3 |  |  |  |  | + | + |  | + | + |
|  | 11 | DB2 |  |  |  |  |  |  |  |  |  |
|  | 15 | 12 |  |  |  |  |  |  |  |  |  |
| 0201 | 7 | DB1 |  |  | + |  |  | + |  |  |  |
|  | 7 | 17 |  |  | + |  |  | + |  |  |  |
|  | 7 | 11 |  |  |  | + |  | + |  |  |  |
| 0301 | 4 | 4(7) |  |  |  |  |  |  |  |  |  |
|  | 4 | 13.2(7) |  |  |  |  |  |  |  |  |  |
|  | 4 | 4(8) |  |  |  | + |  | + |  |  |  |
|  | 4 | 10(8) |  |  |  | + |  | + |  |  |  |
|  | 4 | 13.1(8) |  |  |  | + |  | + |  |  |  |
|  | 4 | 14(8) |  |  |  | + |  | + |  |  |  |
|  | 4 | KT2 |  |  |  |  |  |  |  |  |  |
|  | 4 | 15 |  |  |  |  |  |  |  |  |  |
|  | 9 | 23 |  |  | + |  | + |  |  |  |  |
| 0401 | 8 | 8.1 | (+) |  |  |  | + | + | + | + |  |
|  | 8 | 8.2 | (+) |  |  |  | + | + | + | + |  |
|  | 3 | RSH |  |  |  |  |  |  |  |  |  |
| 0501 | 3 | 3,24 | (+) |  |  |  |  | + |  | + |  |
|  | 3 | 3,25 | (+) |  |  |  |  | + |  | + |  |
|  | 11 | 5 | (+) |  |  |  |  | + |  | + |  |
|  | 11 | 5(9104) | (+)| + |  |  |  |  | + |  | + |  |
|  | 14 | 16 | (+) |  |  |  |  | + |  | + |  |
|  | 12 | DB6 | (+) |  |  |  |  | + |  | + |  |
|  | 16 | 22 | (+) |  |  |  |  | + |  | + |  |
| 0601 | 8 | 8.3 | (+) |  |  |  |  | + |  | + |  |

| | | | DdeI | | | | | | | |
|---|---|---|---|---|---|---|---|---|---|---|
| PDLP | DR | Dw | 650/520 | 450/420 | 410/400 | 390/300 | 200/190 | 150/90 | 80/60 | 50 |
| 0101 | 1 | 1 |  |  | + |  | + | + | + |  |
|  | 1 | 20 |  |  | + |  | + | + | + |  |
|  | 14 | 9 |  |  | + |  | + | + | + |  |
| 0102 | 15 | 2 | + | + |  |  | + | + | + |  |
|  | 16 | 21 |  | + |  |  | + | + | + |  |
|  | 13 | 19 |  |  |  | + | + | + | + |  |
| 0103 | 13 | 18,24 |  |  |  |  |  |  |  |  |
|  | 13 | 18,25 |  |  |  |  |  |  |  |  |
|  | 8 | 8.3 |  | + |  |  | + | + | + |  |
|  | 11 | DB2 |  |  |  |  |  |  |  |  |
|  | 15 | 12 |  |  |  |  |  |  |  |  |
| 0201 | 7 | DB1 |  |  | + |  | + | + | + |  |
|  | 7 | 17 |  |  | + |  | + | + | + |  |
|  | 7 | 11 |  |  |  | + | + | + | + |  |
| 0301 | 4 | 4(7) |  |  |  |  |  |  |  |  |
|  | 4 | 13.2(7) |  |  |  |  |  |  |  |  |
|  | 4 | 4(8) | + |  |  |  |  | + |  | + |
|  | 4 | 10(8) | + |  |  |  |  | + |  | + |
|  | 4 | 13.1(8) | + |  |  |  |  | + |  | + |
|  | 4 | 14(8) | + |  |  |  |  | + |  | + |
|  | 4 | KT2 |  |  |  |  |  |  |  |  |
|  | 4 | 15 |  |  |  |  |  |  |  |  |
|  | 9 | 23 | + |  |  |  |  | + |  | + |
| 0401 | 8 | 8.1 |  |  |  |  | + + | + + | + + |  |
|  | 8 | 8.2 |  |  |  |  | + + | + + | + + |  |
|  | 3 | RSH |  |  |  |  |  |  |  |  |
| 0501 | 3 | 3,24 |  |  | + | + |  | + | + |  |
|  | 3 | 3,25 |  |  | + | + |  | + | + |  |
|  | 11 | 5 |  |  | + | + |  | + | + |  |
|  | 11 | 5(9104) |  |  | +| + |  | + | + |  |
|  | 14 | 16 |  |  | + | + |  | + | + |  |
|  | 12 | DB6 |  |  | + | + |  | + | + |  |
|  | 16 | 22 |  |  | + | + |  | + | + |  |
| 0601 | 8 | 8.3 |  |  |  |  | + + | + + | + + |  |

-continued

| PDLP | DR | Dw | \multicolumn{9}{c}{MboII} |
|------|----|----|-----|-----|-----|-----|-----|-----|-----|-----|-----|
|      |    |    | 390/385 | 380/370 | 365/360 | 350/340 | 335/330 | 305/300 | 250/190 | 180/170 | 140/130 |
| 0101 | 1  | 1  |     |     |     |     | +   |     | +   |     |     |
|      | 1  | 20 |     |     |     |     | +   |     | +   |     |     |
|      | 14 | 9  |     |     |     |     | +   | +   |     |     |     |
| 0102 | 15 | 2  |     |     | +   |     |     | +   |     |     |     |
|      | 16 | 21 |     |     | +   |     |     | +   |     |     |     |
|      | 13 | 19 |     |     | +   |     |     | +   |     |     |     |
| 0103 | 13 | 18,24 |  |     |     |     |     |     |     |     |     |
|      | 13 | 18,25 |  |     |     | +   |     |     |     | +   | +   |
|      | 8  | 8.3 |    |     |     | +   |     |     |     | +   | +   |
|      | 11 | DB2 |    |     |     |     |     |     |     |     |     |
|      | 15 | 12  |    |     |     |     |     |     |     |     |     |
| 0201 | 7  | DB1 |    |     |     | +   |     |     |     | +   | +   |
|      | 7  | 17  |    |     |     | +   |     |     |     | +   | +   |
|      | 7  | 11  |    |     |     | +   |     |     |     | +   | +   |
| 0301 | 4  | 4(7) |   |     |     |     |     |     |     |     |     |
|      | 4  | 13.2(7) | |   |     |     |     |     |     |     |     |
|      | 4  | 4(8) |   |     |     |     |     |     | +   | +   | +   |
|      | 4  | 10(8) |  |     |     |     |     |     | +   | +   | +   |
|      | 4  | 13.1(8) ||     |     |     |     |     |     |     |     |
|      | 4  | 14(8) |  |     |     |     |     |     | +   | +   | +   |
|      | 4  | KT2 |    |     |     |     |     |     |     |     |     |
|      | 4  | 15  |    |     |     |     |     |     |     |     |     |
|      | 9  | 23  |    |     |     |     |     |     | +   | +   | +   |
| 0401 | 8  | 8.1 |    |     |     |     | +   | +   |     |     |     |
|      | 8  | 8.2 |    |     |     | +   |     | +   |     |     |     |
|      | 3  | RSH |    |     |     |     |     |     |     |     |     |
| 0501 | 3  | 3,24 | + | +   |     |     | +   |     |     |     |     |
|      | 3  | 3,25 | + | +   |     |     | +   |     |     |     |     |
|      | 11 | 5   | +  | +   |     |     | +   |     |     |     |     |
|      | 11 | 5(9104) | + | + |     |     | +   |     |     |     | + + |
|      | 14 | 16  |    |     |     | +   |     |     | +   |     |     |
|      | 12 | DB6 | +  | +   |     |     | +   |     |     |     |     |
|      | 16 | 22  |    |     |     |     |     |     |     |     |     |
| 0601 | 8  | 8.3 |    |     |     |     |     | +   |     |     |     |
| PDLP | DR | Dw  | 385/390 | 370/380 | 360/365 | 340/350 | 330/335 | 300/305 | 190/250 | 170/180 | 130/140 |

---

What is claimed is:

1. A genomic mapping method for identifying informative, polymorphic markers and using said markers to identify a chromosomal region associated with a trait, comprising:

(a) obtaining a first set of genomic DNA samples from a plurality of individuals representing the diversity of a general population;

(b) amplifying a non-coding sequence from a selected chromosomal region in each of said first set of genomic DNA samples to produce a first set of amplified DNA sequences;

(c) analyzing said first set of amplified DNA sequences to determine whether said non-coding sequence comprises a plurality of polymorphic regions, wherein said plurality of polymorphic regions defines a plurality of haplotypic patterns detectable by a selected technique for analyzing genetic variation;

(d) determining the number of haplotypic patterns associated with said non-coding sequence that are distinct as measured by said selected technique, wherein each haplotypic pattern is a marker for a haplotype of said selected chromosomal region;

(e) repeating steps (a)–(d) to identify a plurality of non-coding sequences, each having a plurality of associated haplotypic patterns, at a series of selected chromosomal regions;

(f) obtaining a second set of genomic DNA samples from a plurality of individuals with the trait from said general population, wherein said plurality of individuals with the trait is not derived from a single family;

(g) amplifying said plurality of non-coding sequences from said series of selected chromosomal regions in each genomic DNA sample in said second set to produce a second set of amplified DNA sequences;

(h) detecting the haplotypic pattern for each amplified DNA sequence in said second set to identify the haplotype of each corresponding selected chromosomal region;

(i) determining the degree of restriction in haplotype heterogeneity at each selected chromosomal region for said second set of amplified DNA sequences by comparing the number of haplotypic patterns identified for each selected chromosomal region for said first set of amplified DNA sequences and said second set of amplified DNA sequences; and (j) comparing the degree of haplotype heterogeneity restriction across said selected chromosomal regions, to identify a subseries of adjacent selected chromosomal regions having a greater degree of haplotype heterogeneity restriction at a central selected chromosomal region in said subseries than at selected chromosomal regions at the ends of said subseries as an indication that said central selected chromosomal region is associated with the trait.

2. The method of claim 1 wherein each amplified DNA sequence is about 200–2000 bases in length.

3. The method of claim 1 wherein said selected chromosomal regions are about 0.01 to 2 million basepairs (Mbp) apart.

4. The method of claim 3 wherein said individuals are humans.

5. The method of claim 1 wherein said non-coding sequence is an intron sequence.

6. The method of claim 5 additionally comprising the step of identifying said intron sequence by a method selected from the group consisting of:
   (a) comparing the nucleotide sequence of a region of genomic DNA with the nucleotide sequence of a cDNA; and
   (b) producing an amplified genomic DNA sequence having a greater length than a corresponding amplified cDNA sequence.

7. The method of claim 6 wherein said intron sequence is identified after identifying a transcribed region by a method selected from the group consisting of:
   (a) exon trapping;
   (b) zoo blot analysis; and
   (c) use of a restriction endonuclease to identify a CpG island.

8. The method of claim 1 wherein said non-coding sequence is in a region of genomic DNA having a known nucleotide sequence corresponding to a sequence-tagged site or a restriction fragment length polymorphism site.

9. A genomic mapping method for identifying a chromosomal region associated with a trait, comprising:
   (a) obtaining genomic DNA samples from a plurality of individuals with the trait from a general population, wherein said plurality of individuals with the trait is not derived from a single family;
   (b) amplifying a plurality of non-coding sequences from a series of selected chromosomal regions in each genomic DNA sample to produce a plurality of amplified DNA sequences, wherein each selected chromosomal region comprises a plurality of polymorphic non-coding regions, and said plurality of polymorphic non-coding regions defines a plurality of haplotypic patterns detectable by a selected technique for analyzing genetic variation;
   (c) analyzing said plurality of amplified DNA sequences to identify the haplotype of each corresponding selected chromosomal region;
   (d) determining the degree of restriction in haplotype heterogeneity at each selected chromosomal region for said plurality of individuals with the trait, as compared to said general population; and
   (e) comparing the degree of haplotype heterogeneity restriction across said selected chromosomal regions to identify a subseries of adjacent selected chromosomal regions having a greater degree of haplotype heterogeneity restriction at a central selected chromosomal region in said subseries than at selected chromosomal regions at the ends of said subseries as an indication that said central selected chromosomal region is associated with the trait.

10. The method of claim 9 wherein the trait is a monogenic disease.

11. The method of claim 9 wherein the trait is a multigenic disease.

12. The method of claim 9 wherein said plurality of individuals is a group of 20–100 individuals.

13. The method of claim 9 wherein each amplified DNA sequence is about 200–2000 bases in length.

14. The method of claim 9 wherein said selected chromosomal regions are about 0.01 to 2 million basepairs (Mbp) apart.

15. The method of claim 14 wherein said individuals are humans.

16. The method of claim 9 wherein, for at least one selected chromosomal region, said plurality of non-coding polymorphic regions is located in an intron sequence.

17. The method of claim 9 wherein said selected technique for analyzing genetic variation comprises amplification with a haplotype, allele-, or sequence-specific primer.

18. The method of claim 9 wherein at least two of said distinct haplotypic patterns are distinguished on the basis of a difference in the length of two amplified DNA sequences.

19. The method of claim 9 wherein at least two of said distinct haplotypic patterns are distinguished on the basis of a difference in the fragment patterns produced from two amplified DNA sequences following digestion with at least one restriction endonuclease.

20. The method of claim 19 wherein the difference in the fragment patterns is a difference in the number of fragments.

21. The method of claim 19 wherein the difference in the fragment patterns is a difference in the length of at least one fragment.

22. The method of claim 1 wherein the polymorphic regions comprise polymorphic sites.

23. The method of claim 9 wherein the polymorphic regions comprise polymorphic sites.

* * * * *